US011345971B2

(12) United States Patent
Yasuda et al.

(10) Patent No.: US 11,345,971 B2
(45) Date of Patent: May 31, 2022

(54) PRIMER SET FOR DETECTING SARS-COV-2, METHOD FOR TESTING SARS-COV-2, AND REAGENT AND KIT OF TESTING SARS-COV-2

(71) Applicants: NAGASAKI UNIVERSITY, Nagasaki (JP); CANON MEDICAL SYSTEMS CORPORATION, Otawara (JP)

(72) Inventors: Jiro Yasuda, Nagasaki (JP); Rokusuke Yoshikawa, Nagasaki (JP); Haruka Abe, Nagasaki (JP)

(73) Assignees: NAGASAKI UNIVERSITY, Nagasaki (JP); CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/489,049

(22) Filed: Sep. 29, 2021

(65) Prior Publication Data

US 2022/0010389 A1 Jan. 13, 2022

Related U.S. Application Data

(63) Continuation of application No. PCT/JP2020/023401, filed on Jun. 15, 2020.

(51) Int. Cl.

| | |
|---|---|
| ***C12Q 1/70*** | (2006.01) |
| ***C12Q 1/68*** | (2018.01) |
| ***C12Q 1/6876*** | (2018.01) |
| ***G01N 21/78*** | (2006.01) |
| ***C07H 21/04*** | (2006.01) |

(52) U.S. Cl.
CPC .................................... *C12Q 1/701* (2013.01)

(58) Field of Classification Search
CPC ............ C12Q 1/6844; C12Q 2525/301; C12Q 2525/161; C12Q 2527/101; C12Q 2537/143
See application file for complete search history.

(56) References Cited

FOREIGN PATENT DOCUMENTS

JP 5740112 B2 5/2015

OTHER PUBLICATIONS

International Search Report dated Sep. 1, 2020 in PCT/JP2020/023401, 2 pages.
Notification of Reasons for Refusal dated Apr. 1, 2021, issued in Japanese Patent Application No. 2020-564506.
Dandan Li et al. "Primer design for quantitative real-time PCR for the emerging Coronavirus SARS-COV-2". Theranostics 2020, vol. 10, Issue 16, pp. 7150-7162. DOI: 10.7150/Thno. 47649.
Hamid Reza Mollaei et al. "Comparison five primer sets from different genome region of COVID-19 for detection of virus infection by conventional RT-PCR." Iranian Journal of Microbiology. vol 12, No. 3, pp. 185-193, May 29, 2020.
Daniel K.W. Chu et al. "Molecular Diagnosis of a Novel Coronavirus (2019-nCOV) Causing an Outbreak of Pneumonia." Clinical Chemistry. vol. 66, No. 4, pp. 549-555. DOI: 10.1093/clinchem/hraa029, Apr. 2020.
Deguo Wang. "One-pot Detection of COVID-19 with Real-time Reverse-transcription Loop-mediated Isothermal Amplification (RT-LAMP) Assay and Visual RT-LAMP Assay." bioRxiv. DOI: 10.1101/2020.04.21. 052530.
Pazhanimuthu Annamalai. "A Simple Colorimetric Molecular Detection of Novel Coronavirus (COVID-19), An Essential Diagnostic Tool for Pandemic Screening." MedRxiv. DOI: 10.1101/2020.04.10. 20060293.

*Primary Examiner* — Barry A Chestnut
(74) *Attorney, Agent, or Firm* — Oblon, McClelland, Maier & Neustadt, L.L.P.

(57) ABSTRACT

One embodiment according to the present invention relates to a primer set for detecting SARS-CoV-2, the set comprising a plurality of LAMP primers targeting one or more open reading frame (ORF) regions in a SARS-CoV-2 genome, wherein the one or more ORF regions are selected from the group consisting of Orf1b, OrfM, OrfN, and OrfS; and a technique relating to use of this primer set.

16 Claims, 7 Drawing Sheets

Specification includes a Sequence Listing.

FIG. 1 cgggtttgcggtgtaagtgcagcccgtcttacaccgtgcggcacaggcactagtactgatgtcgtatacagggcttttga
catctacaatgataaagtagctggttttgctaaattcctaaaaactaattgttgtcgcttccaagaaaaggacgaagatg
acaatttaattgattcttactttgtagttaagagacacactttctctaactaccaacatgaagaaacaatttataattta
cttaaggattgtccagctgttgctaaacatgacttctttaagtttagaatagacggtgacatggtaccacatatatcacg
tcaacgtcttactaaatacacaatggcagacctcgtctatgctttaaggcattttgatgaaggtaattgtgacacattaa
aagaaatacttgtcacatacaattgttgtgatgatgattatttcaataaaaaggactggtatgattttgtagaaaaccca
gatatattacgcgtatacgccaacttaggtgaacgtgtacgccaagctttgttaaaaacagtacaattctgtgatgccat
gcgaaatgctggtattgttggtgtactgacattagataatcaagatctcaatggtaactggtatgatttcggtgatttca
tacaaaccacgccaggtagtggagttcctgttgtagattcttattattcattgttaatgcctatattaaccttgaccagg
gctttaactgcagagtcacatgttgacactgacttaacaaagccttacattaagtgggatttgttaaaatatgacttcac
ggaagagaggttaaaactctttgaccgttattttaaatattgggatcagacataccacccaaattgtgttaactgtttgg
atgacagatgcattctgcattgtgcaaactttaatgtttattctctacagtgttcccacctacaagttttggaccacta
gtgagaaaaatatttgttgatggtgttccatttgtagtttcaactggataccacttcagagagctaggtgttgtacataa
tcaggatgtaaacttacatagctctagacttagttttaaggaattacttgtgtatgctgctgaccctgctatgcacgctg
cttctggtaatctattactagataaacgcactacgtgcttttcagtagctgcacttactaacaatgttgcttttcaaact
gtcaaacccggtaattttaacaaagacttctatgactttgctgtgtctaagggtttctttaaggaaggaagttctgttga
attaaaacacttcttctttgctcaggatggtaatgctgctatcagcgattatgactactatcgttataatctaccaacaa
tgtgtgatatcagacaactactatttgtagttgaagttgttgataagtactttgattgttacgatggtggctgtattaat
gctaaccaagtcatcgtcaacaacctagacaaatcagctggttttccatttaataaatggggtaaggctagactttatta
tgattcaatgagttatgaggatcaagatgcacttttcgcatatacaaaacgtaatgtcatccctactataactcaaatga
atcttaagtatgccattagtgcaaagaatagagctcgcaccgtagctggtgtctctatctgtagtactatgaccaataga
cagtttcatcaaaaattattgaaatcaatagccgccactagaggagctactgtagtaattggaacaagcaaattctatgg
tggttggcacaacatgttaaaaactgtttatagtgatgtagaaaaccctcaccttatgggttgggattatcctaaatgtg
atagagccatgcctaacatgcttagaattatggcctcacttgttcttgctcgcaaacatacaacgtgttgtagcttgtca
caccgtttctatagattagctaatgagtgtgctcaagtattgagtgaaatggtcatgtgtggcggttcactatatgttaa
accaggtggaacctcatcaggagatgccacaactgcttatgctaatagtgtttttaacatttgtcaagctgtcacggcca
atgttaatgcacttttatctactgatggtaacaaaattgccgataagtatgtccgcaatttacaacacagactttatgag
tgtctctatagaaatagagatgttgacacagactttgtgaatgagttttacgcatatttgcgtaaacatttctcaatgat
gatactctctgacgatgctgttgtgtgtttcaatagcacttatgcatctcaaggtctagtggctagcataaagaacttta
agtcagttctttattatcaaaacaatgtttttatgtctgaagcaaaatgttggactgagactgaccttactaaaggacct
catgaattttgctctcaacatacaatgctagttaaacagggtgatgattatgtgtaccttccttacccagatccatcaag
aatcctaggggccggctgttttgtagatgatatcgtaaaaacagatggtacacttatgattgaacggttcgtgtctttag
ctatagatgcttacccacttactaaacatcctaatcaggagtatgctgatgtctttcatttgtacttacaatacataaga
aagctacatgatgagttaacaggacacatgttagacatgtattctgttatgcttactaatgataacacttcaaggtattg
ggaacctgagttttatgaggctatgtacacaccgcatacagtcttacaggctgttggggcttgtgttctttgcaattcac
agacttcattaagatgtggtgcttgcatacgtagaccattcttatgttgtaaatgctgttacgaccatgtcatatcaaca
tcacataaattagtcttgtctgttaatccgtatgtttgcaatgctccaggttgtgatgtcacagatgtgactcaacttta
cttaggaggtatgagctattattgtaaatcacataaaccacccattagttttccattgtgtgctaatggacaagttttg
gtttatataaaaatacatgtgttggtagcgataatgttactgactttaatgcaattgcaacatgtgactggacaaatgct
ggtgattacattttagctaacacctgtactgaaagactcaagcttttgcagcagaaacgctcaaagctactgaggagac
atttaaactgtcttatggtattgctactgtacgtgaagtgctgtctgacagagaattacatctttcatgggaagttggta
aacctagaccaccacttaaccgaaattatgtctttactggttatcgtgtaactaaaaacagtaaagtacaaataggagag
tacacctttgaaaaaggtgactatggtgatgctgttgtttaccgaggtacaacaacttacaaattaaatgttggtgatta
ttttgtgctgacatcacatacagtaatgccattaagtgcacctacactagtgccacaagagcactatgttagaattactg
gcttatacccaacactcaatatctcagatgagttttctagcaatgttgcaaattatcaaaaggttggtatgcaaaagtat
tctacactccagggaccacctggtactggtaagagtcattttgctattggcctagctctctactacccttctgctcgcat
agtgtatacagcttgctctcatgccgctgttgatgcactatgtgagaaggcattaaaatatttgcctatagataaatgta
gtagaattatacctgcacgtgctcgtgtagagtgttttgataaattcaaagtgaattcaacattagaacagtatgtcttt
tgtactgtaaatgcattgcctgagacgacagcagatatagttgtctttgatgaaatttcaatggccacaaattatgattt
gagtgttgtcaatgccagattacgtgctaagcactatgtgtacattggcgaccctgctcaattacctgcaccacgcacat
tgctaactaagggcacactagaaccagaatatttcaattcagtgtgtagacttatgaaaactataggtccagacatgttc (Full-length: SEQ ID NO:2; Underlined portion: SEQ ID NO:3)

FIG. 2 ctcggaacttgtcggcgttgtcctgctgaaattgttgacactgtgagtgctttggtttatgataataagcttaaagcaca
taaagacaaatcagctcaatgctttaaaatgttttataagggtgttatcacgcatgatgtttcatctgcaattaacaggc
cacaaataggcgtggtaagagaattccttacacgtaaccctgcttggagaaaagctgtctttatttcaccttataattca
cagaatgctgtagcctcaaagatttgggactaccaactcaaactgttgattcatcacagggctcagaatatgactatgt
catattcactcaaaccactgaaacagctcactcttgtaatgtaaacagatttaatgttgctattaccagagcaaaagtag
gcatactttgcataatgtctgatagagacctttatgacaagttgcaatttacaagtcttgaaattccacgtaggaatgtg
gcaactttacaagctgaaaatgtaacaggactctttaaagattgtagtaaggtaatcactgggttacatcctacacaggc
acctacacacctcagtgttgacactaaattcaaaactgaaggtttatgtgttgacatacctggcatacctaaggacatga
cctatagaagactcatctctatgatgggttttaaaatgaattatcaagttaatggttaccctaacatgtttatcacccgc
gaagaagctataagacatgtacgtgcatggattggcttcgatgtcgaggggtgtcatgctactagagaagctgttggtac
caatttacctttacagctaggtttttctacaggtgttaacctagttgctgtacctacaggttatgttgatacacctaata
atacagatttttccagagttagtgctaaaccaccgcctggagatcaatttaaacacctcataccacttatgtacaaagga
cttccttggaatgtagtgcgtataaagattgtacaaatgttaagtgacacacttaaaaatctctctgacagagtcgtatt
tgtcttatgggcacatggctttgagttgacatctatgaagtattttgtgaaaataggacctgagcgcacctgttgtctat
gtgatagacgtgccacatgctttccactgcttcagacacttatgcctgttggcatcattctattggatttgattacgtc
tataatccgtttatgattgatgttcaacaatggggttttacaggtaacctacaaagcaaccatgatctgtattgtcaagt
ccatggtaatgcacatgtagctagttgtgatgcaatcatgactaggtgtctagctgtccacgagtgctttgttaagcgtg
ttgactggactattgaatatcctataattggtgatgaactgaagattaatgcggcttgtagaaaggttcaacacatggtt
gttaaagctgcattattagcagacaaattcccagttcttcacgacattggtaaccctaaagctattaagtgtgtacctca
agctgatgtagaatggaagttctatgatgcacagccttgtagtgacaaagcttataaaatagaagaattattctattctt
atgccacacattctgacaaattcacagatggtgtatgcctatttggaattgcaatgtcgatagatatcctgctaattcc
attgtttgtagatttgacactagagtgctatctaaccttaacttgcctggttgtgatggtggcagtttgtatgtaaataa
acatgcattccacacaccagcttttgataaaagtgcttttgttaatttaaaacaattaccatttttctattactctgaca
gtccatgtgagtctcatggaaaacaagtagtgtcagatatagattatgtaccactaaagtctgctacgtgtataacacgt
tgcaatttaggtggtgctgtctgtagacatcatgctaatgagtacagattgtatctcgatgcttataacatgatgatctc
agctggctttagcttgtgggtttacaaacaatttgatacttataacctctggaacactttacaagacttcagagtttag
aaaatgtggcttttaatgttgtaaataagggacactttgatggacaacagggtgaagtaccagtttctatcattaataac
actgtttacacaaaagttgatggtgttgatgtagaattgtttgaaaataaaacaacattacctgttaatgtagcatttga
gctttgggctaagcgcaacattaaaccagtaccagaggtgaaaatactcaataatttgggtgtggacattgctgctaata
ctgtgatctgggactacaaaagagatgctccagcacatatatctactattggtgtttgttctatgactgacatagccaag
aaaccaactgaaacgatttgtgcaccactcactgtctttttgatggtagagttgatggtcaagtagacttatttagaaa
tgcccgtaatggtgttcttattacagaaggtagtgttaaaggtttacaaccatctgtaggtcccaaacaagctagtctta
atggagtcacattaattggagaagccgtaaaaacacagttcaattattataagaaagttgatggtgttgtccaacaatta
cctgaaacttactttactcagagtagaaatttacaagaatttaaacccaggagtcaaatggaaattgatttcttagaatt
agctatggatgaattcattgaacggtataaattagaaggctatgccttcgaacatatcgtttatggagatttagtcata
gtcagttaggtggtttacatctactgattggactagctaaacgttttaaggaatcaccttttgaattagaagattttatt
cctatggacagtacagttaaaaactatttcataacagatgcgcaaacaggttcatctaagtgtgtgtgttctgttattga
tttattacttgatgattttgttgaaataataaaatcccaagatttatctgtagtttctaaggttgtcaaagtgactattg
actatacagaaatttcatttatgctttggtgtaaagatggccatgtagaaacattttacccaaaattacaatctagtcaa
gcgtggcaaccgggtgttgctatgcctaatctttacaaaatgcaaagaatgctattagaaaagtgtgaccttcaaaatta
tggtgatagtgcaacattacctaaaggcataatgatgaatgtcgcaaaatatactcaactgtgtcaatatttaaacacat
taacattagctgtaccctataatatgagagttatacattttggtgctggttctgataaaggagttgcaccaggtacagct
gttttaagacagtggttgcctacgggtacgctgcttgtcgattcagatcttaatgactttgtctctgatgcagattcaac
tttgattggtgattgtgcaactgtacatacagctaataaatgggatctcattattagtgatatgtacgaccctaagacta
aaaatgttacaaaagaaaatgactctaaagagggtttttcacttacatttgtgggtttatacaacaaaagctagctctt
ggaggttccgtggctataaagataacagaacattcttggaatgctgatctttataagctcatgggacacttcgcatggtg
gacagcctttgttactaatgtgaatgcgtcatcatctgaagcattttaattggatgtaattatcttggcaaaccacgcg
aacaaatagatggttatgtcatgcatgcaaattacatatttggaggaatacaaatccaattcagttgtcttcctattct
ttatttgacatgagtaaatttccccttaaattaaggggtactgctgttatgtctttaaaagaaggtcaaatcaatgatat
gattttatctcttcttagtaaaggtagacttataattagagaaaacaacagagttgttatttctagtgatgttcttgtta
acaactaa (Full-length: SEQ ID NO:4; Underlined portion: SEQ ID NO:5)

FIG. 3 atggcagattccaacggtactattaccgttgaagagcttaaaaagctccttgaacaatggaacctagtaataggtttcct
attccttacatggatttgtcttctacaatttgcctatgccaacaggaataggttttgtatataattaagttaattttcc
tctggctgttatggccagtaactttagcttgttttgtgcttgctgctgtttacagaataaattggatcaccggtggaatt
gctatcgcaatggcttgtcttgtaggcttgatgtggctcagctacttcattgcttctttcagactgtttgcgcgtacgcg
ttccatgtggtcattcaatccagaaactaacattcttctcaacgtgccactccatggcactattctgaccagaccgcttc
tagaaagtgaactcgtaatcggagctgtgatccttcgtggacatcttcgtattgctggacaccatctaggacgctgtgac
atcaaggacctgcctaaagaaatcactgttgctacatcacgaacgctttcttattacaaattgggagcttcgcagcgtgt
agcaggtgactcaggttttgctgcatacagtcgctacaggattggcaactataaattaaacacagaccattccagtagca
gtgacaatattgctttgcttgtacagtaa (Full-length: SEQ ID NO:6; Underlined portion: SEQ ID NO:7)

FIG. 4 atgtctgataatggaccccaaaatcagcgaaatgcaccccgcattacgtttggtggaccctcagattcaactggcagtaa
ccagaatggagaacgcagtggggcgcgatcaaaacaacgtcggccccaaggtttacccaataatactgcgtcttggttca
ccgctctcactcaacatggcaaggaagaccttaaattccctcgaggacaaggcgttccaattaacaccaatagcagtcca
gatgaccaaattggctactaccgaagagctaccagacgaattcgtggtggtgacggtaaaatgaaagatctcagtccaag
atggtatttctactacctaggaactgggccagaagctggacttccctatggtgctaacaaagacggcatcatatgggttg
caactgagggagccttgaatacaccaaaagatcacattggcacccgcaatcctgctaacaatgctgcaatcgtgctacaa
cttcctcaaggaacaacattgccaaaaggcttctacgcagaagggagcagaggcggcagtcaagcctcttctcgttcctc
atcacgtagtcgcaacagttcaagaaattcaactccaggcagcagtaggggaacttctcctgctagaatggctggcaatg
gcggtgatgctgctcttgctttgctgctgcttgacagattgaaccagcttgagagcaaaatgtctggtaaaggccaacaa
caacaaggccaaactgtcactaagaaatctgctgctgaggcttctaagaagcctcggcaaaaacgtactgccactaaagc
atacaatgtaacacaagctttcggcagacgtggtccagaacaaacccaaggaaattttggggaccaggaactaatcagac
aaggaactgattacaaacattggccgcaaattgcacaatttgcccccagcgcttcagcgttcttcggaatgtcgcgcatt
ggcatggaagtcacaccttcgggaacgtggttgacctacacaggtgccatcaaattggatgacaaagatccaaatttcaa
agatcaagtcattttgctgaataagcatattgacgcatacaaaacattcccaccaacagagcctaaaaaggacaaaaaga
agaaggctgatgaaactcaagccttaccgcagagacagaagaaacagcaaactgtgactcttcttcctgctgcagatttg
gatgatttctccaaacaattgcaacaatccatgagcagtgctgactcaactcaggcctaa (Full-length: SEQ ID NO:8; Underlined portion: SEQ ID NO:9)

FIG. 5 atgtttgtttttcttgttttattgccactagtctctagtcagtgtgttaatcttacaaccagaactcaattaccccctgc
atacactaattctttcacacgtggtgtttattaccctgacaaagttttcagatcctcagttttacattcaactcaggact
tgttcttacctttcttttccaatgttacttggttccatgctatacatgtctctgggaccaatggtactaagaggtttgat
aaccctgtcctaccatttaatgatggtgtttattttgcttccactgagaagtctaacataataagaggctggatttttgg
tactactttagattcgaagacccagtccctacttattgttaataacgctactaatgttgttattaaagtctgtgaatttc
aattttgtaatgatccatttttgggtgtttattaccacaaaaacaacaaaagttggatggaaagtgagttcagagtttat
tctagtgcgaataattgcacttttgaatatgtctctcagccttttcttatggaccttgaaggaaaacagggtaatttcaa
aaatcttagggaatttgtgtttaagaatattgatggttattttaaaatatattctaagcacacgcctattaatttagtgc
gtgatctccctcagggtttttcggctttagaaccattggtagatttgccaataggtattaacatcactaggtttcaaact
ttacttgctttacatagaagttatttgactcctggtgattcttcttcaggttggacagctggtgctgcagcttattatgt
gggttatcttcaacctaggacttttctattaaaatataatgaaaatggaaccattacagatgctgtagactgtgcacttg
accctctctcagaaacaaagtgtacgttgaaatccttcactgtagaaaaaggaatctatcaaacttctaactttagagtc
caaccaacagaatctattgttagatttcctaatattacaaacttgtgcccttttggtgaagtttttaacgccaccagatt
tgcatctgtttatgcttggaacaggaagagaatcagcaactgtgttgctgattattctgtcctatataattccgcatcat
tttccacttttaagtgttatggagtgtctcctactaaattaaatgatctctgctttactaatgtctatgcagattcattt
gtaattagaggtgatgaagtcagacaaatcgctccagggcaaactggaaagattgctgattataattataaattaccaga
tgattttacaggctgcgttatagcttggaattctaacaatcttgattctaaggttggtggtaattataattacctgtata
gattgtttaggaagtctaatctcaaaccttttgagagagatatttcaactgaaatctatcaggccggtagcacaccttgt
aatggtgttgaaggttttaattgttactttcctttacaatcatatggtttccaacccactaatggtgttggttaccaacc
atacagagtagtagtactttctttgaacttctacatgcaccagcaactgtttgtggacctaaaaagtctactaatttgg
ttaaaaacaaatgtgtcaatttcaacttcaatggtttaacaggcacaggtgttcttactgagtctaacaaaaagtttctg
cctttccaacaatttggcagagacattgctgacactactgatgctgtccgtgatccacagacacttgagattcttgacat
tacaccatgttcttttggtggtgtcagtgttataacaccaggaacaaatacttctaaccaggttgctgttctttatcagg
atgttaactgcacagaagtccctgttgctattcatgcagatcaacttactcctacttggcgtgtttattctacaggttct
aatgtttttcaaacacgtgcaggctgtttaataggggctgaacatgtcaacaactcatatgagtgtgacatacccattgg
tgcaggtatatgcgctagttatcagactcagactaattctcctcggcgggcacgtagtgtagctagtcaatccatcattg
cctacactatgtcacttggtgcagaaaattcagttgcttactctaataactctattgccatacccacaaattttactatt
agtgttaccacagaaattctaccagtgtctatgaccaagacatcagtagattgtacaatgtacatttgtggtgattcaac
tgaatgcagcaatcttttgttgcaatatggcagtttttgtacacaattaaaccgtgctttaactggaatagctgttgaac
aagacaaaaacacccaagaagtttttgcacaagtcaaacaaatttacaaaacaccaccaattaaagattttggtggtttt
aatttttcacaaatattaccagatccatcaaaaccaagcaagaggtcatttattgaagatctacttttcaacaaagtgac
acttgcagatgctggcttcatcaaacaatatggtgattgccttggtgatattgctgctagagacctcatttgtgcacaaa
agtttaacggccttactgttttgccacctttgctcacagatgaaatgattgctcaatacacttctgcactgttagcgggt
acaatcacttctggttggacctttggtgcaggtgctgcattacaaataccatttgctatgcaaatggcttataggtttaa
tggtattggagttacacagaatgttctctatgagaaccaaaaattgattgccaaccaatttaatagtgctattggcaaaa
ttcaagactcactttcttccacagcaagtgcacttggaaaacttcaagatgtggtcaaccaaaatgcacaagctttaaac
acgcttgttaaacaacttagctccaattttggtgcaatttcaagtgttttaaatgatatcctttcacgtcttgacaaagt
tgaggctgaagtgcaaattgataggttgatcacaggcagacttcaaagtttgcagacatatgtgactcaacaattaatta
gagctgcagaaatcagagcttctgctaatcttgctgctactaaaatgtcagagtgtgtacttggacaatcaaaaagagtt
gattttgtggaaagggctatcatcttatgtccttccctcagtcagcacctcatggtgtagtcttcttgcatgtgactta
tgtccctgcacaagaaaagaacttcacaactgctcctgccatttgtcatgatggaaaagcacactttcctcgtgaaggtg
tctttgtttcaaatggcacacactggtttgtaacacaaaggaattttatgaaccacaaatcattactacagacaacaca
tttgtgtctggtaactgtgatgttgtaataggaattgtcaacaacacagtttatgatcctttgcaacctgaattagactc
attcaaggaggagttagataaatattttaagaatcatacatcaccagatgttgatttaggtgacatctctggcattaatg
cttcagttgtaaacattcaaaaagaaattgaccgcctcaatgaggttgccaagaatttaaatgaatctctcatcgatctc
caagaacttggaaagtatgagcagtatataaaatggccatggtacatttggctaggttttatagctggcttgattgccat
agtaatggtgacaattatgctttgctgtatgaccagttgctgtagttgtctcaagggctgttgttcttgtggatcctgct
gcaaatttgatgaagacgactctgagccagtgctcaaaggagtcaaattacattacacataa (Full-length: SEQ ID NO:10; First underlined portion: SEQ ID NO:11;
Second underlined portion: SEQ ID NO:12)

SEQUENCE LISTING

```
<160> NUMBER OF SEQ ID NOS: 52

<210> SEQ ID NO 1
<211> LENGTH: 8088
<212> TYPE: DNA
<213> ORGANISM: SARS-CoV-2

<400> SEQUENCE: 1

cgggtttgcg gtgtaagtgc agcccgtctt acaccgtgcg gcacaggcac tagtactgat      60

gtcgtataca gggcttttga catctacaat gataaagtag ctggttttgc taaattccta     120

aaaactaatt gttgtcgctt ccaagaaaag gacgaagatg acaatttaat tgattcttac     180

tttgtagtta agagacacac tttctctaac taccaacatg aagaaacaat ttataattta     240

cttaaggatt gtccagctgt tgctaaacat gacttcttta agtttagaat agacggtgac     300

atggtaccac atatatcacg tcaacgtctt actaaataca caatggcaga cctcgtctat     360

gctttaaggc attttgatga aggtaattgt gacacattaa aagaaatact tgtcacatac     420

aattgttgtg atgatgatta tttcaataaa aaggactggt atgattttgt agaaaaccca     480

gatatattac gcgtatacgc caacttaggt gaacgtgtac gccaagcttt gttaaaaaca     540

gtacaattct gtgatgccat gcgaaatgct ggtattgttg gtgtactgac attagataat     600

caagatctca atggtaactg gtatgatttc ggtgatttca tacaaaccac gccaggtagt     660

ggagttcctg ttgtagattc ttattattca ttgttaatgc ctatattaac cttgaccagg     720

gctttaactg cagagtcaca tgttgacact gacttaacaa agccttacat taagtgggat     780

ttgttaaaat atgacttcac ggaagagagg ttaaaactct ttgaccgtta ttttaaatat     840

tgggatcaga cataccaccc aaattgtgtt aactgtttgg atgacagatg cattctgcat     900

tgtgcaaact ttaatgtttt attctctaca gtgttcccac ctacaagttt tggaccacta     960

gtgagaaaaa tatttgttga tggtgttcca tttgtagttt caactggata ccacttcaga    1020
```

-continued

```
gagctaggtg ttgtacataa tcaggatgta aacttacata gctctagact tagttttaag   1080
gaattacttg tgtatgctgc tgaccctgct atgcacgctg cttctggtaa tctattacta   1140
gataaacgca ctacgtgctt ttcagtagct gcacttacta acaatgttgc ttttcaaact   1200
gtcaaacccg gtaattttaa caaagacttc tatgactttg ctgtgtctaa gggtttcttt   1260
aaggaaggaa gttctgttga attaaaacac ttcttctttg ctcaggatgg taatgctgct   1320
atcagcgatt atgactacta tcgttataat ctaccaacaa tgtgtgatat cagacaacta   1380
ctatttgtag ttgaagttgt tgataagtac tttgattgtt acgatggtgg ctgtattaat   1440
gctaaccaag tcatcgtcaa caacctagac aaatcagctg gttttccatt taataaatgg   1500
ggtaaggcta gactttatta tgattcaatg agttatgagg atcaagatgc acttttcgca   1560
tatacaaaac gtaatgtcat ccctactata actcaaatga atcttaagta tgccattagt   1620
gcaaagaata gagctcgcac cgtagctggt gtctctatct gtagtactat gaccaataga   1680
cagtttcatc aaaaattatt gaaatcaata gccgccacta gaggagctac tgtagtaatt   1740
ggaacaagca aattctatgg tggttggcac aacatgttaa aaactgttta tagtgatgta   1800
gaaaaccctc accttatggg ttgggattat cctaaatgtg atagagccat gcctaacatg   1860
cttagaatta tggcctcact tgttcttgct cgcaaacata caacgtgttg tagcttgtca   1920
caccgtttct atagattagc taatgagtgt gctcaagtat tgagtgaaat ggtcatgtgt   1980
ggcggttcac tatatgttaa accaggtgga acctcatcag gagatgccac aactgcttat   2040
gctaatagtg tttttaacat ttgtcaagct gtcacggcca atgttaatgc acttttatct   2100
actgatggta acaaaattgc cgataagtat gtccgcaatt tacaacacag actttatgag   2160
tgtctctata gaaatagaga tgttgacaca gactttgtga atgagtttta cgcatatttg   2220
cgtaaacatt tctcaatgat gatactctct gacgatgctg ttgtgtgttt caatagcact   2280
tatgcatctc aaggtctagt ggctagcata aagaacttta agtcagttct ttattatcaa   2340
aacaatgttt ttatgtctga agcaaaatgt tggactgaga ctgaccttac taaaggacct   2400
catgaatttt gctctcaaca tacaatgcta gttaaacagg gtgatgatta tgtgtacctt   2460
ccttacccag atccatcaag aatcctaggg gccggctgtt ttgtagatga tatcgtaaaa   2520
acagatggta cacttatgat tgaacggttc gtgtctttag ctatagatgc ttacccactt   2580
actaaacatc ctaatcagga gtatgctgat gtctttcatt tgtacttaca atacataaga   2640
aagctacatg atgagttaac aggacacatg ttagacatgt attctgttat gcttactaat   2700
gataacactt caaggtattg ggaacctgag ttttatgagg ctatgtacac accgcataca   2760
gtcttacagg ctgttggggc ttgtgttctt tgcaattcac agacttcatt aagatgtggt   2820
gcttgcatac gtagaccatt cttatgttgt aaatgctgtt acgaccatgt catatcaaca   2880
tcacataaat tagtcttgtc tgttaatccg tatgtttgca atgctccagg ttgtgatgtc   2940
acagatgtga ctcaacttta cttaggaggt atgagctatt attgtaaatc acataaacca   3000
cccattagtt ttccattgtg tgctaatgga caagtttttg gtttatataa aaatacatgt   3060
gttggtagcg ataatgttac tgactttaat gcaattgcaa catgtgactg gacaaatgct   3120
ggtgattaca ttttagctaa cacctgtact gaaagactca agctttttgc agcagaaacg   3180
ctcaaagcta ctgaggagac atttaaactg tcttatggta ttgctactgt acgtgaagtg   3240
ctgtctgaca gagaattaca tctttcatgg gaagttggta aacctagacc accacttaac   3300
cgaaattatg tctttactgg ttatcgtgta actaaaaaca gtaaagtaca aataggagag   3360
```

-continued

```
tacacctttg aaaaaggtga ctatggtgat gctgttgttt accgaggtac aacaacttac   3420
aaattaaatg ttggtgatta ttttgtgctg acatcacata cagtaatgcc attaagtgca   3480
cctacactag tgccacaaga gcactatgtt agaattactg gcttataccc aacactcaat   3540
atctcagatg agttttctag caatgttgca aattatcaaa aggttggtat gcaaaagtat   3600
tctacactcc agggaccacc tggtactggt aagagtcatt ttgctattgg cctagctctc   3660
tactaccctt ctgctcgcat agtgtataca gcttgctctc atgccgctgt tgatgcacta   3720
tgtgagaagg cattaaaata tttgcctata gataaatgta gtagaattat acctgcacgt   3780
gctcgtgtag agtgttttga taaattcaaa gtgaattcaa cattagaaca gtatgtcttt   3840
tgtactgtaa atgcattgcc tgagacgaca gcagatatag ttgtctttga tgaaatttca   3900
atggccacaa attatgattt gagtgttgtc aatgccagat tacgtgctaa gcactatgtg   3960
tacattggcg accctgctca attacctgca ccacgcacat tgctaactaa gggcacacta   4020
gaaccagaat atttcaattc agtgtgtaga cttatgaaaa ctataggtcc agacatgttc   4080
ctcggaactt gtcggcgttg tcctgctgaa attgttgaca ctgtgagtgc tttggtttat   4140
gataataagc ttaaagcaca taaagacaaa tcagctcaat gctttaaaat gttttataag   4200
ggtgttatca cgcatgatgt ttcatctgca attaacaggc cacaaatagg cgtggtaaga   4260
gaattcctta cacgtaaccc tgcttggaga aaagctgtct ttatttcacc ttataattca   4320
cagaatgctg tagcctcaaa gattttggga ctaccaactc aaactgttga ttcatcacag   4380
ggctcagaat atgactatgt catattcact caaaccactg aaacagctca ctcttgtaat   4440
gtaaacagat ttaatgttgc tattaccaga gcaaaagtag gcatactttg cataatgtct   4500
gatagagacc tttatgacaa gttgcaattt acaagtcttg aaattccacg taggaatgtg   4560
gcaactttac aagctgaaaa tgtaacagga ctctttaaag attgtagtaa ggtaatcact   4620
gggttacatc ctacacaggc acctacacac ctcagtgttg acactaaatt caaaactgaa   4680
ggtttatgtg ttgacatacc tggcatacct aaggacatga cctatagaag actcatctct   4740
atgatgggtt ttaaaatgaa ttatcaagtt aatggttacc ctaacatgtt tatcacccgc   4800
gaagaagcta taagacatgt acgtgcatgg attggcttcg atgtcgaggg gtgtcatgct   4860
actagagaag ctgttggtac caatttacct ttacagctag gttttctac aggtgttaac   4920
ctagttgctg tacctacagg ttatgttgat acacctaata atacagattt ttccagagtt   4980
agtgctaaac caccgcctgg agatcaattt aaacacctca taccacttat gtacaaagga   5040
cttccttgga atgtagtgcg tataaagatt gtacaaatgt taagtgacac acttaaaaat   5100
ctctctgaca gagtcgtatt tgtcttatgg gcacatggct ttgagttgac atctatgaag   5160
tattttgtga aaataggacc tgagcgcacc tgttgtctat gtgatagacg tgccacatgc   5220
ttttccactg cttcagacac ttatgcctgt tggcatcatt ctattggatt tgattacgtc   5280
tataatccgt ttatgattga tgttcaacaa tggggtttta caggtaacct acaaagcaac   5340
catgatctgt attgtcaagt ccatggtaat gcacatgtag ctagttgtga tgcaatcatg   5400
actaggtgtc tagctgtcca cgagtgcttt gttaagcgtg ttgactggac tattgaatat   5460
cctataattg gtgatgaact gaagattaat gcggcttgta gaaaggttca acacatggtt   5520
gttaaagctg cattattagc agacaaattc ccagttcttc acgacattgg taaccctaaa   5580
gctattaagt gtgtacctca agctgatgta gaatggaagt tctatgatgc acagccttgt   5640
agtgacaaag cttataaaat agaagaatta ttctattctt atgccacaca ttctgacaaa   5700
ttcacagatg gtgtatgcct attttggaat tgcaatgtcg atagatatcc tgctaattcc   5760
```

-continued

```
attgtttgta gatttgacac tagagtgcta tctaacctta acttgcctgg ttgtgatggt   5820
ggcagtttgt atgtaaataa acatgcattc cacacaccag cttttgataa aagtgctttt   5880
gttaatttaa aacaattacc atttttctat tactctgaca gtccatgtga gtctcatgga   5940
aaacaagtag tgtcagatat agattatgta ccactaaagt ctgctacgtg tataacacgt   6000
tgcaatttag gtggtgctgt ctgtagacat catgctaatg agtacagatt gtatctcgat   6060
gcttataaca tgatgatctc agctggcttt agcttgtggg tttacaaaca atttgatact   6120
tataacctct ggaacacttt tacaagactt cagagtttag aaaatgtggc ttttaatgtt   6180
gtaaataagg gacactttga tggacaacag ggtgaagtac cagtttctat cattaataac   6240
actgtttaca caaaagttga tggtgttgat gtagaattgt ttgaaaataa aacaacatta   6300
cctgttaatg tagcatttga gctttgggct aagcgcaaca ttaaaccagt accagaggtg   6360
aaaatactca ataatttggg tgtggacatt gctgctaata ctgtgatctg ggactacaaa   6420
agagatgctc cagcacatat atctactatt ggtgtttgtt ctatgactga catagccaag   6480
aaaccaactg aaacgatttg tgcaccactc actgtctttt ttgatggtag agttgatggt   6540
caagtagact tatttagaaa tgcccgtaat ggtgttctta ttacagaagg tagtgttaaa   6600
ggtttacaac catctgtagg tcccaaacaa gctagtctta atggagtcac attaattgga   6660
gaagccgtaa aaacacagtt caattattat aagaaagttg atggtgttgt ccaacaatta   6720
cctgaaactt actttactca gagtagaaat ttacaagaat ttaaacccag gagtcaaatg   6780
gaaattgatt tcttagaatt agctatggat gaattcattg aacggtataa attagaaggc   6840
tatgccttcg aacatatcgt ttatggagat tttagtcata gtcagttagg tggtttacat   6900
ctactgattg gactagctaa acgttttaag gaatcacctt ttgaattaga agattttatt   6960
cctatggaca gtacagttaa aaactatttc ataacagatg cgcaaacagg ttcatctaag   7020
tgtgtgtgtt ctgttattga tttattactt gatgatttg ttgaaataat aaaatcccaa    7080
gatttatctg tagtttctaa ggttgtcaaa gtgactattg actatacaga aatttcattt   7140
atgctttggt gtaaagatgg ccatgtagaa acattttacc caaaattaca atctagtcaa   7200
gcgtggcaac cgggtgttgc tatgcctaat ctttacaaaa tgcaaagaat gctattagaa   7260
aagtgtgacc ttcaaaatta tggtgatagt gcaacattac ctaaaggcat aatgatgaat   7320
gtcgcaaaat atactcaact gtgtcaatat ttaaacacat taacattagc tgtaccctat   7380
aatatgagag ttatacattt tggtgctggt tctgataaag gagttgcacc aggtacagct   7440
gttttaagac agtggttgcc tacgggtacg ctgcttgtcg attcagatct taatgacttt   7500
gtctctgatg cagattcaac tttgattggt gattgtgcaa ctgtacatac agctaataaa   7560
tgggatctca ttattagtga tatgtacgac cctaagacta aaaatgttac aaaagaaaat   7620
gactctaaag agggtttttt cacttacatt tgtgggttta tacaacaaaa gctagctctt   7680
ggaggttccg tggctataaa gataacagaa cattcttgga atgctgatct ttataagctc   7740
atgggacact tcgcatggtg gacagccttt gttactaatg tgaatgcgtc atcatctgaa   7800
gcatttttaa ttggatgtaa ttatcttggc aaaccacgcg aacaaataga tggttatgtc   7860
atgcatgcaa attacatatt ttggaggaat acaaatccaa ttcagttgtc ttcctattct   7920
ttatttgaca tgagtaaatt tccccttaaa ttaaggggta ctgctgttat gtctttaaaa   7980
gaaggtcaaa tcaatgatat gattttatct cttcttagta aaggtagact tataattaga   8040
gaaaacaaca gagttgttat ttctagtgat gttcttgtta acaactaa               8088
```

<210> SEQ ID NO 2
<211> LENGTH: 4080
<212> TYPE: DNA
<213> ORGANISM: SARS-CoV-2

<400> SEQUENCE: 2
cgggtttgcg gtgtaagtgc agcccgtctt acaccgtgcg gcacaggcac tagtactgat 60
gtcgtataca gggcttttga catctacaat gataaagtag ctggttttgc taaattccta 120
aaaactaatt gttgtcgctt ccaagaaaag gacgaagatg acaatttaat tgattcttac 180
tttgtagtta agagacacac tttctctaac taccaacatg aagaaacaat ttataattta 240
cttaaggatt gtccagctgt tgctaaacat gacttcttta agtttagaat agacggtgac 300
atggtaccac atatatcacg tcaacgtctt actaaataca caatggcaga cctcgtctat 360
gctttaaggc attttgatga aggtaattgt gacacattaa aagaaatact tgtcacatac 420
aattgttgtg atgatgatta tttcaataaa aaggactggt atgattttgt agaaaaccca 480
gatatattac gcgtatacgc caacttaggt gaacgtgtac gccaagcttt gttaaaaaca 540
gtacaattct gtgatgccat gcgaaatgct ggtattgttg gtgtactgac attagataat 600
caagatctca atggtaactg gtatgatttc ggtgatttca tacaaaccac gccaggtagt 660
ggagttcctg ttgtagattc ttattattca ttgttaatgc ctatattaac cttgaccagg 720
gctttaactg cagagtcaca tgttgacact gacttaacaa agccttacat taagtgggat 780
ttgttaaaat atgacttcac ggaagagagg ttaaaactct ttgaccgtta ttttaaatat 840
tgggatcaga cataccaccc aaattgtgtt aactgtttgg atgacagatg cattctgcat 900
tgtgcaaact ttaatgtttt attctctaca gtgttcccac ctacaagttt tggaccacta 960
gtgagaaaaa tatttgttga tggtgttcca tttgtagttt caactggata ccacttcaga 1020
gagctaggtg ttgtacataa tcaggatgta aacttacata gctctagact tagttttaag 1080
gaattacttg tgtatgctgc tgaccctgct atgcacgctg cttctggtaa tctattacta 1140
gataaacgca ctacgtgctt ttcagtagct gcacttacta acaatgttgc ttttcaaact 1200
gtcaaacccg gtaattttaa caaagacttc tatgactttg ctgtgtctaa gggtttcttt 1260
aaggaaggaa gttctgttga attaaaacac ttcttctttg ctcaggatgg taatgctgct 1320
atcagcgatt atgactacta tcgttataat ctaccaacaa tgtgtgatat cagacaacta 1380
ctatttgtag ttgaagttgt tgataagtac tttgattgtt acgatggtgg ctgtattaat 1440
gctaaccaag tcatcgtcaa caacctagac aaatcagctg gttttccatt taataaatgg 1500
ggtaaggcta gactttatta tgattcaatg agttatgagg atcaagatgc acttttcgca 1560
tatacaaaac gtaatgtcat ccctactata actcaaatga atcttaagta tgccattagt 1620
gcaaagaata gagctcgcac cgtagctggt gtctctatct gtagtactat gaccaataga 1680
cagtttcatc aaaaattatt gaaatcaata gccgccacta gaggagctac tgtagtaatt 1740
ggaacaagca aattctatgg tggttggcac aacatgttaa aaactgttta tagtgatgta 1800
gaaaaccctc accttatggg ttgggattat cctaaatgtg atagagccat gcctaacatg 1860
cttagaatta tggcctcact tgttcttgct cgcaaacata caacgtgttg tagcttgtca 1920
caccgtttct atagattagc taatgagtgt gctcaagtat tgagtgaaat ggtcatgtgt 1980
ggcggttcac tatatgttaa accaggtgga acctcatcag gagatgccac aactgcttat 2040
gctaatagtg tttttaacat ttgtcaagct gtcacggcca atgttaatgc acttttatct 2100
actgatggta acaaaattgc cgataagtat gtccgcaatt tacaacacag actttatgag 2160
tgtctctata gaaatagaga tgttgacaca gactttgtga atgagtttta cgcatatttg 2220
cgtaaacatt tctcaatgat gatactctct gacgatgctg ttgtgtgttt caatagcact 2280
tatgcatctc aaggtctagt ggctagcata aagaacttta agtcagttct ttattatcaa 2340
aacaatgttt ttatgtctga agcaaaatgt tggactgaga ctgaccttac taaaggacct 2400
catgaatttt gctctcaaca tacaatgcta gttaaacagg gtgatgatta tgtgtacctt 2460
ccttacccag atccatcaag aatcctaggg gccggctgtt ttgtagatga tatcgtaaaa 2520
acagatggta cacttatgat tgaacggttc gtgtctttag ctatagatgc ttacccactt 2580
actaaacatc ctaatcagga gtatgctgat gtctttcatt tgtacttaca atacataaga 2640
aagctacatg atgagttaac aggacacatg ttagacatgt attctgttat gcttactaat 2700
gataacactt caaggtattg ggaacctgag ttttatgagg ctatgtacac accgcataca 2760
gtcttacagg ctgttggggc ttgtgttctt tgcaattcac agacttcatt aagatgtggt 2820
gcttgcatac gtagaccatt cttatgttgt aaatgctgtt acgaccatgt catatcaaca 2880
tcacataaat tagtcttgtc tgttaatccg tatgtttgca atgctccagg ttgtgatgtc 2940
acagatgtga ctcaacttta cttaggaggt atgagctatt attgtaaatc acataaacca 3000
cccattagtt ttccattgtg tgctaatgga caagtttttg gtttatataa aaatacatgt 3060
gttggtagcg ataatgttac tgactttaat gcaattgcaa catgtgactg gacaaatgct 3120
ggtgattaca ttttagctaa cacctgtact gaaagactca agctttttgc agcagaaacg 3180
ctcaaagcta ctgaggagac atttaaactg tcttatggta ttgctactgt acgtgaagtg 3240
ctgtctgaca gagaattaca tctttcatgg gaagttggta aacctagacc accacttaac 3300
cgaaattatg tctttactgg ttatcgtgta actaaaaaca gtaaagtaca aataggagag 3360
tacacctttg aaaaaggtga ctatggtgat gctgttgttt accgaggtac aacaacttac 3420
aaattaaatg ttggtgatta ttttgtgctg acatcacata cagtaatgcc attaagtgca 3480
cctacactag tgccacaaga gcactatgtt agaattactg gcttataccc aacactcaat 3540
atctcagatg agttttctag caatgttgca aattatcaaa aggttggtat gcaaaagtat 3600
tctacactcc agggaccacc tggtactggt aagagtcatt ttgctattgg cctagctctc 3660
tactaccctt ctgctcgcat agtgtataca gcttgctctc atgccgctgt tgatgcacta 3720
tgtgagaagg cattaaaata tttgcctata gataaatgta gtagaattat acctgcacgt 3780
gctcgtgtag agtgttttga taaattcaaa gtgaattcaa cattagaaca gtatgtcttt 3840
tgtactgtaa atgcattgcc tgagacgaca gcagatatag ttgtctttga tgaaatttca 3900
atggccacaa attatgattt gagtgttgtc aatgccagat tacgtgctaa gcactatgtg 3960
tacattggcg accctgctca attacctgca ccacgcacat tgctaactaa gggcacacta 4020
gaaccagaat atttcaattc agtgtgtaga cttatgaaaa ctataggtcc agacatgttc 4080

<210> SEQ ID NO 3
<211> LENGTH: 245
<212> TYPE: DNA
<213> ORGANISM: SARS-CoV-2

<400> SEQUENCE: 3
aacctgagtt ttatgaggct atgtacacac cgcatacagt cttacaggct gttggggctt 60
gtgttctttg caattcacag acttcattaa gatgtggtgc ttgcatacgt agaccattct 120
tatgttgtaa atgctgttac gaccatgtca tatcaacatc acataaatta gtcttgtctg 180
ttaatccgta tgtttgcaat gctccaggtt gtgatgtcac agatgtgact caactttact 240
tagga 245

<210> SEQ ID NO 4
<211> LENGTH: 4008
<212> TYPE: DNA
<213> ORGANISM: SARS-CoV-2

<400> SEQUENCE: 4
ctcggaactt gtcggcgttg tcctgctgaa attgttgaca ctgtgagtgc tttggtttat 60
gataataagc ttaaagcaca taaagacaaa tcagctcaat gctttaaaat gttttataag 120
ggtgttatca cgcatgatgt ttcatctgca attaacaggc cacaaatagg cgtggtaaga 180
gaattcctta cacgtaaccc tgcttggaga aaagctgtct ttatttcacc ttataattca 240
cagaatgctg tagcctcaaa gattttggga ctaccaactc aaactgttga ttcatcacag 300
ggctcagaat atgactatgt catattcact caaaccactg aaacagctca ctcttgtaat 360
gtaaacagat ttaatgttgc tattaccaga gcaaaagtag gcatactttg cataatgtct 420
gatagagacc tttatgacaa gttgcaattt acaagtcttg aaattccacg taggaatgtg 480
gcaactttac aagctgaaaa tgtaacagga ctctttaaag attgtagtaa ggtaatcact 540
gggttacatc ctacacaggc acctacacac ctcagtgttg acactaaatt caaaactgaa 600
ggtttatgtg ttgacatacc tggcatacct aaggacatga cctatagaag actcatctct 660
atgatgggtt ttaaaatgaa ttatcaagtt aatggttacc ctaacatgtt tatcacccgc 720
gaagaagcta taagacatgt acgtgcatgg attggcttcg atgtcgaggg gtgtcatgct 780
actagagaag ctgttggtac caatttacct ttacagctag gtttttctac aggtgttaac 840
ctagttgctg tacctacagg ttatgttgat acacctaata atacagattt ttccagagtt 900
agtgctaaac caccgcctgg agatcaattt aaacacctca taccacttat gtacaaagga 960
cttccttgga atgtagtgcg tataaagatt gtacaaatgt taagtgacac acttaaaaat 1020
ctctctgaca gagtcgtatt tgtcttatgg gcacatggct ttgagttgac atctatgaag 1080
tattttgtga aaataggacc tgagcgcacc tgttgtctat gtgatagacg tgccacatgc 1140
ttttccactg cttcagacac ttatgcctgt tggcatcatt ctattggatt tgattacgtc 1200
tataatccgt ttatgattga tgttcaacaa tggggtttta caggtaacct acaaagcaac 1260
catgatctgt attgtcaagt ccatggtaat gcacatgtag ctagttgtga tgcaatcatg 1320
actaggtgtc tagctgtcca cgagtgcttt gttaagcgtg ttgactggac tattgaatat 1380
cctataattg gtgatgaact gaagattaat gcggcttgta gaaaggttca acacatggtt 1440
gttaaagctg cattattagc agacaaattc ccagttcttc acgacattgg taaccctaaa 1500
gctattaagt gtgtacctca agctgatgta gaatggaagt tctatgatgc acagccttgt 1560
agtgacaaag cttataaaat agaagaatta ttctattctt atgccacaca ttctgacaaa 1620
ttcacagatg gtgtatgcct attttggaat tgcaatgtcg atagatatcc tgctaattcc 1680
attgtttgta gatttgacac tagagtgcta tctaacctta acttgcctgg ttgtgatggt 1740
ggcagtttgt atgtaaataa acatgcattc cacacaccag cttttgataa aagtgctttt 1800
gttaatttaa aacaattacc atttttctat tactctgaca gtccatgtga gtctcatgga 1860
aaacaagtag tgtcagatat agattatgta ccactaaagt ctgctacgtg tataacacgt 1920
tgcaatttag gtggtgctgt ctgtagacat catgctaatg agtacagatt gtatctcgat 1980
gcttataaca tgatgatctc agctggcttt agcttgtggg tttacaaaca atttgatact 2040

-continued tataacctct ggaacacttt tacaagactt cagagtttag aaaatgtggc ttttaatgtt 2100
gtaaataagg gacactttga tggacaacag ggtgaagtac cagtttctat cattaataac 2160
actgtttaca caaaagttga tggtgttgat gtagaattgt ttgaaaataa aacaacatta 2220
cctgttaatg tagcatttga gctttgggct aagcgcaaca ttaaaccagt accagaggtg 2280
aaaatactca ataatttggg tgtggacatt gctgctaata ctgtgatctg ggactacaaa 2340
agagatgctc cagcacatat atctactatt ggtgtttgtt ctatgactga catagccaag 2400
aaaccaactg aaacgatttg tgcaccactc actgtctttt ttgatggtag agttgatggt 2460
caagtagact tatttagaaa tgcccgtaat ggtgttctta ttacagaagg tagtgttaaa 2520
ggtttacaac catctgtagg tcccaaacaa gctagtctta atggagtcac attaattgga 2580
gaagccgtaa aaacacagtt caattattat aagaaagttg atggtgttgt ccaacaatta 2640
cctgaaactt actttactca gagtagaaat ttacaagaat ttaaacccag gagtcaaatg 2700
gaaattgatt tcttagaatt agctatggat gaattcattg aacggtataa attagaaggc 2760
tatgccttcg aacatatcgt ttatggagat tttagtcata gtcagttagg tggtttacat 2820
ctactgattg gactagctaa acgttttaag gaatcacctt ttgaattaga agattttatt 2880
cctatggaca gtacagttaa aaactatttc ataacagatg cgcaaacagg ttcatctaag 2940
tgtgtgtgtt ctgttattga tttattactt gatgattttg ttgaaataat aaaatcccaa 3000
gatttatctg tagtttctaa ggttgtcaaa gtgactattg actatacaga aatttcattt 3060
atgctttggt gtaaagatgg ccatgtagaa acattttacc caaaattaca atctagtcaa 3120
gcgtggcaac cgggtgttgc tatgcctaat ctttacaaaa tgcaaagaat gctattagaa 3180
aagtgtgacc ttcaaaatta tggtgatagt gcaacattac ctaaaggcat aatgatgaat 3240
gtcgcaaaat atactcaact gtgtcaatat ttaaacacat taacattagc tgtaccctat 3300
aatatgagag ttatacattt tggtgctggt tctgataaag gagttgcacc aggtacagct 3360
gttttaagac agtggttgcc tacgggtacg ctgcttgtcg attcagatct taatgacttt 3420
gtctctgatg cagattcaac tttgattggt gattgtgcaa ctgtacatac agctaataaa 3480
tgggatctca ttattagtga tatgtacgac cctaagacta aaaatgttac aaaagaaaat 3540
gactctaaag agggtttttt cacttacatt tgtgggttta tacaacaaaa gctagctctt 3600
ggaggttccg tggctataaa gataacagaa cattcttgga atgctgatct ttataagctc 3660
atgggacact tcgcatggtg gacagccttt gttactaatg tgaatgcgtc atcatctgaa 3720
gcatttttaa ttggatgtaa ttatcttggc aaaccacgcg aacaaataga tggttatgtc 3780
atgcatgcaa attacatatt ttggaggaat acaaatccaa ttcagttgtc ttcctattct 3840
ttatttgaca tgagtaaatt tccccttaaa ttaaggggta ctgctgttat gtctttaaaa 3900
gaaggtcaaa tcaatgatat gattttatct cttcttagta aaggtagact tataattaga 3960
gaaaacaaca gagttgttat ttctagtgat gttcttgtta acaactaa 4008

<210> SEQ ID NO 5
<211> LENGTH: 256
<212> TYPE: DNA
<213> ORGANISM: SARS-CoV-2

<400> SEQUENCE: 5
ggttttttca cttacatttg tgggtttata caacaaaagc tagctcttgg aggttccgtg 60
gctataaaga taacagaaca ttcttggaat gctgatcttt ataagctcat gggacacttc 120

-continued

```
gcatggtgga cagcctttgt tactaatgtg aatgcgtcat catctgaagc atttttaatt    180

ggatgtaatt atcttggcaa accacgcgaa caaatagatg gttatgtcat gcatgcaaat    240

tacatatttt ggagga                                                    256


<210> SEQ ID NO 6
<211> LENGTH: 669
<212> TYPE: DNA
<213> ORGANISM: SARS-CoV-2

<400> SEQUENCE: 6

atggcagatt ccaacggtac tattaccgtt gaagagctta aaaagctcct tgaacaatgg     60

aacctagtaa taggtttcct attccttaca tggatttgtc ttctacaatt tgcctatgcc    120

aacaggaata ggtttttgta tataattaag ttaattttcc tctggctgtt atggccagta    180

actttagctt gttttgtgct tgctgctgtt tacagaataa attggatcac cggtggaatt    240

gctatcgcaa tggcttgtct tgtaggcttg atgtggctca gctacttcat tgcttctttc    300

agactgtttg cgcgtacgcg ttccatgtgg tcattcaatc cagaaactaa cattcttctc    360

aacgtgccac tccatggcac tattctgacc agaccgcttc tagaaagtga actcgtaatc    420

ggagctgtga tccttcgtgg acatcttcgt attgctggac accatctagg acgctgtgac    480

atcaaggacc tgcctaaaga aatcactgtt gctacatcac gaacgctttc ttattacaaa    540

ttgggagctt cgcagcgtgt agcaggtgac tcaggttttg ctgcatacag tcgctacagg    600

attggcaact ataaattaaa cacagaccat tccagtagca gtgacaatat tgctttgctt    660

gtacagtaa                                                            669


<210> SEQ ID NO 7
<211> LENGTH: 215
<212> TYPE: DNA
<213> ORGANISM: SARS-CoV-2

<400> SEQUENCE: 7

ttctttcaga ctgtttgcgc gtacgcgttc catgtggtca ttcaatccag aaactaacat     60

tcttctcaac gtgccactcc atggcactat tctgaccaga ccgcttctag aaagtgaact    120

cgtaatcgga gctgtgatcc ttcgtggaca tcttcgtatt gctggacacc atctaggacg    180

ctgtgacatc aaggacctgc ctaaagaaat cactg                               215


<210> SEQ ID NO 8
<211> LENGTH: 1260
<212> TYPE: DNA
<213> ORGANISM: SARS-CoV-2

<400> SEQUENCE: 8

atgtctgata atggacccca aaatcagcga aatgcacccc gcattacgtt tggtggaccc     60

tcagattcaa ctggcagtaa ccagaatgga gaacgcagtg gggcgcgatc aaaacaacgt    120

cggccccaag gtttacccaa taatactgcg tcttggttca ccgctctcac tcaacatggc    180

aaggaagacc ttaaattccc tcgaggacaa ggcgttccaa ttaacaccaa tagcagtcca    240

gatgaccaaa ttggctacta ccgaagagct accagacgaa ttcgtggtgg tgacggtaaa    300

atgaaagatc tcagtccaag atggtatttc tactacctag gaactgggcc agaagctgga    360

cttccctatg gtgctaacaa agacggcatc atatgggttg caactgaggg agccttgaat    420

acaccaaaag atcacattgg cacccgcaat cctgctaaca atgctgcaat cgtgctacaa    480

cttcctcaag gaacaacatt gccaaaaggc ttctacgcag aagggagcag aggcggcagt    540
```

caagcctctt ctcgttcctc atcacgtagt cgcaacagtt caagaaattc aactccaggc 600
agcagtaggg gaacttctcc tgctagaatg gctggcaatg gcggtgatgc tgctcttgct 660
ttgctgctgc ttgacagatt gaaccagctt gagagcaaaa tgtctggtaa aggccaacaa 720
caacaaggcc aaactgtcac taagaaatct gctgctgagg cttctaagaa gcctcggcaa 780
aaacgtactg ccactaaagc atacaatgta acacaagctt tcggcagacg tggtccagaa 840
caaacccaag gaaattttgg ggaccaggaa ctaatcagac aaggaactga ttacaaacat 900
tggccgcaaa ttgcacaatt tgcccccagc gcttcagcgt tcttcggaat gtcgcgcatt 960
ggcatggaag tcacaccttc gggaacgtgg ttgacctaca caggtgccat caaattggat 1020
gacaaagatc caaatttcaa agatcaagtc attttgctga ataagcatat tgacgcatac 1080
aaaacattcc caccaacaga gcctaaaaag gacaaaaaga agaaggctga tgaaactcaa 1140
gccttaccgc agagacagaa gaaacagcaa actgtgactc ttcttcctgc tgcagatttg 1200
gatgatttct ccaaacaatt gcaacaatcc atgagcagtg ctgactcaac tcaggcctaa 1260

<210> SEQ ID NO 9
<211> LENGTH: 231
<212> TYPE: DNA
<213> ORGANISM: SARS-CoV-2

<400> SEQUENCE: 9
gccaaaaggc ttctacgcag aagggagcag aggcggcagt caagcctctt ctcgttcctc 60
atcacgtagt cgcaacagtt caagaaattc aactccaggc agcagtaggg gaacttctcc 120
tgctagaatg gctggcaatg gcggtgatgc tgctcttgct ttgctgctgc ttgacagatt 180
gaaccagctt gagagcaaaa tgtctggtaa aggccaacaa caacaaggcc a 231

<210> SEQ ID NO 10
<211> LENGTH: 3822
<212> TYPE: DNA
<213> ORGANISM: SARS-CoV-2

<400> SEQUENCE: 10
atgtttgttt ttcttgtttt attgccacta gtctctagtc agtgtgttaa tcttacaacc 60
agaactcaat taccccctgc atacactaat tctttcacac gtggtgttta ttaccctgac 120
aaagttttca gatcctcagt tttacattca actcaggact tgttcttacc tttcttttcc 180
aatgttactt ggttccatgc tatacatgtc tctgggacca atggtactaa gaggtttgat 240
aaccctgtcc taccatttaa tgatggtgtt tattttgctt ccactgagaa gtctaacata 300
ataagaggct ggatttttgg tactacttta gattcgaaga cccagtccct acttattgtt 360
aataacgcta ctaatgttgt tattaaagtc tgtgaatttc aattttgtaa tgatccattt 420
ttgggtgttt attaccacaa aaacaacaaa agttggatgg aaagtgagtt cagagtttat 480
tctagtgcga ataattgcac ttttgaatat gtctctcagc cttttcttat ggaccttgaa 540
ggaaaacagg gtaatttcaa aaatcttagg gaatttgtgt ttaagaatat tgatggttat 600
tttaaaatat attctaagca cacgcctatt aatttagtgc gtgatctccc tcagggtttt 660
tcggctttag aaccattggt agatttgcca ataggtatta acatcactag gtttcaaact 720
ttacttgctt tacatagaag ttatttgact cctggtgatt cttcttcagg ttggacagct 780
ggtgctgcag cttattatgt gggttatctt caacctagga cttttctatt aaaatataat 840
gaaaatggaa ccattacaga tgctgtagac tgtgcacttg accctctctc agaaacaaag 900

```
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
ctacttttca acaaagtgac acttgcagat gctggcttca tcaaacaata tggtgattgc   2520
cttggtgata ttgctgctag agacctcatt tgtgcacaaa agtttaacgg ccttactgtt   2580
ttgccacctt tgctcacaga tgaaatgatt gctcaataca cttctgcact gttagcgggt   2640
acaatcactt ctggttggac ctttggtgca ggtgctgcat tacaaatacc atttgctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acagcaagtg cacttggaaa acttcaagat gtggtcaacc aaaatgcaca agctttaaac   2880
acgcttgtta aacaacttag ctccaatttt ggtgcaattt caagtgtttt aaatgatatc   2940
ctttcacgtc ttgacaaagt tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
```

cactggtttg taacacaaag gaatttttat gaaccacaaa tcattactac agacaacaca 3360
tttgtgtctg gtaactgtga tgttgtaata ggaattgtca acaacacagt ttatgatcct 3420
ttgcaacctg aattagactc attcaaggag gagttagata aatattttaa gaatcataca 3480
tcaccagatg ttgatttagg tgacatctct ggcattaatg cttcagttgt aaacattcaa 3540
aaagaaattg accgcctcaa tgaggttgcc aagaatttaa atgaatctct catcgatctc 3600
caagaacttg gaaagtatga gcagtatata aaatggccat ggtacatttg gctaggtttt 3660
atagctggct tgattgccat agtaatggtg acaattatgc tttgctgtat gaccagttgc 3720
tgtagttgtc tcaagggctg ttgttcttgt ggatcctgct gcaaatttga tgaagacgac 3780
tctgagccag tgctcaaagg agtcaaatta cattacacat aa 3822

<210> SEQ ID NO 11
<211> LENGTH: 229
<212> TYPE: DNA
<213> ORGANISM: SARS-CoV-2

<400> SEQUENCE: 11
ttggcagaga cattgctgac actactgatg ctgtccgtga tccacagaca cttgagattc 60
ttgacattac accatgttct tttggtggtg tcagtgttat aacaccagga acaaatactt 120
ctaaccaggt tgctgttctt tatcaggatg ttaactgcac agaagtccct gttgctattc 180
atgcagatca acttactcct acttggcgtg tttattctac aggttctaa 229

<210> SEQ ID NO 12
<211> LENGTH: 266
<212> TYPE: DNA
<213> ORGANISM: SARS-CoV-2

<400> SEQUENCE: 12
tattgctgct agagacctca tttgtgcaca aaagtttaac ggccttactg ttttgccacc 60
tttgctcaca gatgaaatga ttgctcaata cacttctgca ctgttagcgg gtacaatcac 120
ttctggttgg acctttggtg caggtgctgc attacaaata ccatttgcta tgcaaatggc 180
ttataggttt aatggtattg gagttacaca gaatgttctc tatgagaacc aaaaattgat 240
tgccaaccaa tttaatagtg ctattg 266

<210> SEQ ID NO 13
<211> LENGTH: 23
<212> TYPE: DNA
<213> ORGANISM: Artificial Sequence
<220> FEATURE:
<223> OTHER INFORMATION: F3 primer which targets partial region of Orf1b
(SEQ ID NO. 5) on SARS-CoV-2 genome

<400> SEQUENCE: 13 ggtttttca cttacatttg tgg 23

<210> SEQ ID NO 14
<211> LENGTH: 23
<212> TYPE: DNA
<213> ORGANISM: Artificial Sequence
<220> FEATURE:
<223> OTHER INFORMATION: B3 primer which targets partial region of Orf1b
(SEQ ID NO. 5) on SARS-CoV-2 genome

<400> SEQUENCE: 14
tcctccaaaa tatgtaattt gca 23

```
<210> SEQ ID NO 15
<211> LENGTH: 44
<212> TYPE: DNA
<213> ORGANISM: Artificial Sequence
<220> FEATURE:
<223> OTHER INFORMATION: FIP primer which targets partial region of
      Orf1b (SEQ ID NO. 5) on SARS-CoV-2 genome

<400> SEQUENCE: 15

gcgaagtgtc ccatgagctt ataaactagc tcttggaggt tccg                  44


<210> SEQ ID NO 16
<211> LENGTH: 47
<212> TYPE: DNA
<213> ORGANISM: Artificial Sequence
<220> FEATURE:
<223> OTHER INFORMATION: BIP primer which targets partial region of
      Orf1b (SEQ ID NO. 5) on SARS-CoV-2 genome

<400> SEQUENCE: 16

aatgcgtcat catctgaagc attttcataa ccatctattt gttcgcg               47


<210> SEQ ID NO 17
<211> LENGTH: 23
<212> TYPE: DNA
<213> ORGANISM: Artificial Sequence
<220> FEATURE:
<223> OTHER INFORMATION: LF primer which targets partial region of Orf1b
      (SEQ ID NO. 5) on SARS-CoV-2 genome

<400> SEQUENCE: 17

tcagcattcc aagaatgttc tgt                                          23


<210> SEQ ID NO 18
<211> LENGTH: 26
<212> TYPE: DNA
<213> ORGANISM: Artificial Sequence
<220> FEATURE:
<223> OTHER INFORMATION: LB primer which targets partial region of Orf1b
      (SEQ ID NO. 5) on SARS-CoV-2 genome

<400> SEQUENCE: 18

attggatgta attatcttgg caaacc                                       26


<210> SEQ ID NO 19
<211> LENGTH: 20
<212> TYPE: DNA
<213> ORGANISM: Artificial Sequence
<220> FEATURE:
<223> OTHER INFORMATION: F3 primer which targets partial region of Orf1b
      (SEQ ID NO. 3) on SARS-CoV-2 genome

<400> SEQUENCE: 19

aacctgagtt ttatgaggct                                              20


<210> SEQ ID NO 20
<211> LENGTH: 22
<212> TYPE: DNA
<213> ORGANISM: Artificial Sequence
<220> FEATURE:
<223> OTHER INFORMATION: B3 primer which targets partial region of Orf1b
      (SEQ ID NO. 3) on SARS-CoV-2 genome

<400> SEQUENCE: 20

tcctaagtaa agttgagtca ca                                           22
```

-continued

<210> SEQ ID NO 21
<211> LENGTH: 45
<212> TYPE: DNA
<213> ORGANISM: Artificial Sequence
<220> FEATURE:
<223> OTHER INFORMATION: FIP primer which targets partial region of Orf1b (SEQ ID NO. 3) on SARS-CoV-2 genome

<400> SEQUENCE: 21
tgcaagcacc acatcttaat gaagtcgcat acagtcttac aggct 45

<210> SEQ ID NO 22
<211> LENGTH: 44
<212> TYPE: DNA
<213> ORGANISM: Artificial Sequence
<220> FEATURE:
<223> OTHER INFORMATION: BIP primer which targets partial region of Orf1b (SEQ ID NO. 3) on SARS-CoV-2 genome

<400> SEQUENCE: 22
acgaccatgt catatcaaca tcacaacatc acaacctgga gcat 44

<210> SEQ ID NO 23
<211> LENGTH: 20
<212> TYPE: DNA
<213> ORGANISM: Artificial Sequence
<220> FEATURE:
<223> OTHER INFORMATION: LF primer which targets partial region of Orf1b (SEQ ID NO. 3) on SARS-CoV-2 genome

<400> SEQUENCE: 23
caaagaacac aagccccaac 20

<210> SEQ ID NO 24
<211> LENGTH: 26
<212> TYPE: DNA
<213> ORGANISM: Artificial Sequence
<220> FEATURE:
<223> OTHER INFORMATION: LB primer which targets partial region of Orf1b (SEQ ID NO. 3) on SARS-CoV-2 genome

<400> SEQUENCE: 24
gtcttgtctg ttaatccgta tgtttg 26

<210> SEQ ID NO 25
<211> LENGTH: 19
<212> TYPE: DNA
<213> ORGANISM: Artificial Sequence
<220> FEATURE:
<223> OTHER INFORMATION: F3 primer which targets partial region of Orf1b (SEQ ID NO. 7) on SARS-CoV-2 genome

<400> SEQUENCE: 25
ttctttcaga ctgtttgcg 19

<210> SEQ ID NO 26
<211> LENGTH: 21
<212> TYPE: DNA
<213> ORGANISM: Artificial Sequence
<220> FEATURE:
<223> OTHER INFORMATION: B3 primer which targets partial region of Orf1b (SEQ ID NO. 7) on SARS-CoV-2 genome

<400> SEQUENCE: 26
cagtgatttc tttaggcagg t 21

<210> SEQ ID NO 27

<211> LENGTH: 41
<212> TYPE: DNA
<213> ORGANISM: Artificial Sequence
<220> FEATURE:
<223> OTHER INFORMATION: FIP primer which targets partial region of
Orf1b (SEQ ID NO. 7) on SARS-CoV-2 genome

<400> SEQUENCE: 27
ggtcagaata gtgccatgga gtgtacgcgt tccatgtggt c 41

<210> SEQ ID NO 28
<211> LENGTH: 43
<212> TYPE: DNA
<213> ORGANISM: Artificial Sequence
<220> FEATURE:
<223> OTHER INFORMATION: BIP primer which targets partial region of
Orf1b (SEQ ID NO. 7) on SARS-CoV-2 genome

<400> SEQUENCE: 28
accgcttcta gaaagtgaac tcgtcagcgt cctagatggt gtc 43

<210> SEQ ID NO 29
<211> LENGTH: 25
<212> TYPE: DNA
<213> ORGANISM: Artificial Sequence
<220> FEATURE:
<223> OTHER INFORMATION: LF primer which targets partial region of Orf1b
(SEQ ID NO. 7) on SARS-CoV-2 genome

<400> SEQUENCE: 29
gcacgttgag aagaatgtta gtttc 25

<210> SEQ ID NO 30
<211> LENGTH: 19
<212> TYPE: DNA
<213> ORGANISM: Artificial Sequence
<220> FEATURE:
<223> OTHER INFORMATION: LB primer which targets partial region of Orf1b
(SEQ ID NO. 7) on SARS-CoV-2 genome

<400> SEQUENCE: 30
cggagctgtg atccttcgt 19

<210> SEQ ID NO 31
<211> LENGTH: 18
<212> TYPE: DNA
<213> ORGANISM: Artificial Sequence
<220> FEATURE:
<223> OTHER INFORMATION: F3 primer which targets partial region of Orf1b
(SEQ ID NO. 9) on SARS-CoV-2 genome

<400> SEQUENCE: 31
gccaaaaggc ttctacgc 18

<210> SEQ ID NO 32
<211> LENGTH: 18
<212> TYPE: DNA
<213> ORGANISM: Artificial Sequence
<220> FEATURE:
<223> OTHER INFORMATION: B3 primer which targets partial region of Orf1b
(SEQ ID NO. 9) on SARS-CoV-2 genome

<400> SEQUENCE: 32
tggccttgtt gttgttgg 18

<210> SEQ ID NO 33
<211> LENGTH: 44

<212> TYPE: DNA
<213> ORGANISM: Artificial Sequence
<220> FEATURE:
<223> OTHER INFORMATION: FIP primer which targets partial region of Orf1b (SEQ ID NO. 9) on SARS-CoV-2 genome

<400> SEQUENCE: 33
cctactgctg cctggagttg aatcagtcaa gcctcttctc gttc 44

<210> SEQ ID NO 34
<211> LENGTH: 43
<212> TYPE: DNA
<213> ORGANISM: Artificial Sequence
<220> FEATURE:
<223> OTHER INFORMATION: BIP primer which targets partial region of Orf1b (SEQ ID NO. 9) on SARS-CoV-2 genome

<400> SEQUENCE: 34
gctagaatgg ctggcaatgg cgacattttg ctctcaagct ggt 43

<210> SEQ ID NO 35
<211> LENGTH: 25
<212> TYPE: DNA
<213> ORGANISM: Artificial Sequence
<220> FEATURE:
<223> OTHER INFORMATION: LF primer which targets partial region of Orf1b (SEQ ID NO. 9) on SARS-CoV-2 genome

<400> SEQUENCE: 35
cttgaactgt tgcgactacg tgatg 25

<210> SEQ ID NO 36
<211> LENGTH: 22
<212> TYPE: DNA
<213> ORGANISM: Artificial Sequence
<220> FEATURE:
<223> OTHER INFORMATION: LB primer which targets partial region of Orf1b (SEQ ID NO. 9) on SARS-CoV-2 genome

<400> SEQUENCE: 36
gctttgctgc tgcttgacag at 22

<210> SEQ ID NO 37
<211> LENGTH: 18
<212> TYPE: DNA
<213> ORGANISM: Artificial Sequence
<220> FEATURE:
<223> OTHER INFORMATION: F3 primer which targets partial region of Orf1b (SEQ ID NO. 11) on SARS-CoV-2 genome

<400> SEQUENCE: 37
ttggcagaga cattgctg 18

<210> SEQ ID NO 38
<211> LENGTH: 23
<212> TYPE: DNA
<213> ORGANISM: Artificial Sequence
<220> FEATURE:
<223> OTHER INFORMATION: B3 primer which targets partial region of Orf1b (SEQ ID NO. 11) on SARS-CoV-2 genome

<400> SEQUENCE: 38
ttagaacctg tagaataaac acg 23

<210> SEQ ID NO 39
<211> LENGTH: 42
<212> TYPE: DNA

<213> ORGANISM: Artificial Sequence
<220> FEATURE:
<223> OTHER INFORMATION: FIP primer which targets partial region of Orf1b (SEQ ID NO. 11) on SARS-CoV-2 genome

<400> SEQUENCE: 39
gacaccacca aaagaacatg gtgctactga tgctgtccgt ga 42

<210> SEQ ID NO 40
<211> LENGTH: 47
<212> TYPE: DNA
<213> ORGANISM: Artificial Sequence
<220> FEATURE:
<223> OTHER INFORMATION: BIP primer which targets partial region of Orf1b (SEQ ID NO. 11) on SARS-CoV-2 genome

<400> SEQUENCE: 40
ccaggttgct gttctttatc aggataggag taagttgatc tgcatga 47

<210> SEQ ID NO 41
<211> LENGTH: 24
<212> TYPE: DNA
<213> ORGANISM: Artificial Sequence
<220> FEATURE:
<223> OTHER INFORMATION: LF primer which targets partial region of Orf1b (SEQ ID NO. 11) on SARS-CoV-2 genome

<400> SEQUENCE: 41
tcaagaatct caagtgtctg tgga 24

<210> SEQ ID NO 42
<211> LENGTH: 20
<212> TYPE: DNA
<213> ORGANISM: Artificial Sequence
<220> FEATURE:
<223> OTHER INFORMATION: LB primer which targets partial region of Orf1b (SEQ ID NO. 11) on SARS-CoV-2 genome

<400> SEQUENCE: 42
gcacagaagt ccctgttgct 20

<210> SEQ ID NO 43
<211> LENGTH: 20
<212> TYPE: DNA
<213> ORGANISM: Artificial Sequence
<220> FEATURE:
<223> OTHER INFORMATION: F3 primer which targets partial region of Orf1b (SEQ ID NO. 12) on SARS-CoV-2 genome

<400> SEQUENCE: 43
tattgctgct agagacctca 20

<210> SEQ ID NO 44
<211> LENGTH: 24
<212> TYPE: DNA
<213> ORGANISM: Artificial Sequence
<220> FEATURE:
<223> OTHER INFORMATION: B3 primer which targets partial region of Orf1b (SEQ ID NO. 12) on SARS-CoV-2 genome

<400> SEQUENCE: 44
caatagcact attaaattgg ttgg 24

<210> SEQ ID NO 45
<211> LENGTH: 41
<212> TYPE: DNA
<213> ORGANISM: Artificial Sequence -continued
<220> FEATURE:
<223> OTHER INFORMATION: FIP primer which targets partial region of
Orf1b (SEQ ID NO. 12) on SARS-CoV-2 genome

<400> SEQUENCE: 45
gtacccgcta acagtgcaga agggccttac tgttttgcca c 41

<210> SEQ ID NO 46
<211> LENGTH: 49
<212> TYPE: DNA
<213> ORGANISM: Artificial Sequence
<220> FEATURE:
<223> OTHER INFORMATION: BIP primer which targets partial region of
Orf1b (SEQ ID NO. 12) on SARS-CoV-2 genome

<400> SEQUENCE: 46
caggtgctgc attacaaata ccatttagag aacattctgt gtaactcca 49

<210> SEQ ID NO 47
<211> LENGTH: 24
<212> TYPE: DNA
<213> ORGANISM: Artificial Sequence
<220> FEATURE:
<223> OTHER INFORMATION: LF primer which targets partial region of Orf1b
(SEQ ID NO. 12) on SARS-CoV-2 genome

<400> SEQUENCE: 47
tgagcaatca tttcatctgt gagc 24

<210> SEQ ID NO 48
<211> LENGTH: 24
<212> TYPE: DNA
<213> ORGANISM: Artificial Sequence
<220> FEATURE:
<223> OTHER INFORMATION: LB primer which targets partial region of Orf1b
(SEQ ID NO. 12) on SARS-CoV-2 genome

<400> SEQUENCE: 48
tgctatgcaa atggcttata ggtt 24

<210> SEQ ID NO 49
<211> LENGTH: 20
<212> TYPE: DNA
<213> ORGANISM: Artificial Sequence
<220> FEATURE:
<223> OTHER INFORMATION: Forward primer which targets E gene on
SARS-CoV-2 genome and which is used in NIID recommended protocol

<400> SEQUENCE: 49
aaattttggg gaccaggaac 20

<210> SEQ ID NO 50
<211> LENGTH: 20
<212> TYPE: DNA
<213> ORGANISM: Artificial Sequence
<220> FEATURE:
<223> OTHER INFORMATION: Reverse primer which targets E gene on
SARS-CoV-2 genome and which is used in NIID recommended protocol

<400> SEQUENCE: 50
tggcacctgt gtaggtcaac 20

<210> SEQ ID NO 51
<211> LENGTH: 26
<212> TYPE: DNA
<213> ORGANISM: Artificial Sequence
<220> FEATURE:

-continued

```
<223> OTHER INFORMATION: Forward primer which targets E gene on
      SARS-CoV-2 genome and which is used in WHO recommended protocol

<400> SEQUENCE: 51

acaggtacgt taatagttaa tagcgt                                       26


<210> SEQ ID NO 52
<211> LENGTH: 22
<212> TYPE: DNA
<213> ORGANISM: Artificial Sequence
<220> FEATURE:
<223> OTHER INFORMATION: Reverse primer which targets E gene on
      SARS-CoV-2 genome and which is used in WHO recommended protocol

<400> SEQUENCE: 52

atattgcagc agtacgcaca ca                                           22
```

PRIMER SET FOR DETECTING SARS-COV-2, METHOD FOR TESTING SARS-COV-2, AND REAGENT AND KIT OF TESTING SARS-COV-2

CROSS-REFERENCE TO RELATED APPLICATION

This application is based upon and claims the benefit of priority from International Patent Application No. PCT/JP2020/023401, filed on Jun. 15, 2020; the entire contents of which are incorporated herein by reference.

FIELD

Embodiments described herein generally relate to a primer set for detecting SARS-CoV-2, a method for testing SARS-CoV-2, and a reagent and kit of testing SARS-CoV-2.

BACKGROUND

COVID-19, which is a novel coronavirus infectious disease, was first recognized in 2019 around Wuhan City in China. Thereafter, this was propagated world-widely as a novel infectious disease. COVID-19 is confirmed to be the infectious disease caused by the coronavirus SARS-CoV-2 (Severe Acute Respiratory Syndrome Coronavirus 2).

SARS-CoV-2 is the envelope virus that has a single-strand plus chain RNA genome, belonging to the SARS-related coronaviruses (SARSr-CoV) of the genus *Betacoronavirus*. This virus is not considered to be a direct descendant of SARS-CoV, which is the SARS coronavirus that prevailed in China in 2003; but this virus is named SARS-CoV-2 due to SARS-CoV.

At present, for technology of detecting the coronavirus by specifically amplifying nucleic acids derived from the coronavirus, RT-PCR method is practiced. In fact, the RT-PCR method was promptly practiced in the detection of SARS-CoV-2, too. However, in consideration of the pretreatment time of specimen, detection of the coronavirus by means of the RT-PCR method takes a long time (typically about 6 to 8 hours) and lacks promptness. In order to enable prompt detection of the coronavirus by specific amplification of the nucleic acids derived from the coronavirus, technologies using a LAMP method that uses a specific primer set is reported (Patent Literature 1).

BRIEF DESCRIPTION OF DRAWINGS

FIG. 1 illustrates the partial nucleotide sequence of an Orf1b portion (SEQ ID NO:2) corresponding to the nucleotide sequence at positions 1 to 4,080 in the nucleotide sequence that encodes the Orf1b in the SARS-CoV-2 genome (SEQ ID NO:1). The underlined portion indicates the nucleotide sequence that encodes the first partial region (245 base length) (SEQ ID NO:3) amplified by the LAMP primers in Example.

FIG. 2 illustrates the partial nucleotide sequence of an Orf1b portion (SEQ ID NO:4) corresponding to the nucleotide sequence at positions 4,081 to 8,088 in the nucleotide sequence that encodes the Orf1b in the SARS-CoV-2 genome (SEQ ID NO:1). The underlined portion indicates the nucleotide sequence that encodes the second partial region (256 base length) (SEQ ID NO:5) amplified by the LAMP primers in Example.

FIG. 3 illustrates the nucleotide sequence that encodes OrfM (SEQ ID NO:6) in the SARS-CoV-2 genome. The underlined portion indicates the nucleotide sequence that encodes the region (215 base length) (SEQ ID NO:7) amplified by the LAMP primers in Example.

FIG. 4 illustrates the nucleotide sequence that encodes OrfN (SEQ ID NO:8) in the SARS-CoV-2 genome. The underlined portion indicates the nucleotide sequence that encodes the region (231 base length) (SEQ ID NO:9) amplified by the LAMP primers in Example.

FIG. 5 illustrates the nucleotide sequence that encodes OrfS (SEQ ID NO:10) in the SARS-CoV-2 genome. The underlined portions indicate the nucleotide sequence that encodes the first part region (229 base length) (SEQ ID NO:11), and the nucleotide sequence that encodes the second part region (266 base length) (SEQ ID NO:12), which are amplified by the LAMP primers in Example.

DETAILED DESCRIPTION

One embodiment according to the present invention relates to a primer set for detecting SARS-CoV-2, the primer set comprising a plurality of LAMP primers targeting one or more Open Reading Frame (ORF) regions in the SARS-CoV-2 genome. The one or more ORF regions to be targeted are selected from the group consisting of Orf1b, OrfM, OrfN, and OrfS.

The SARS-CoV-2 genome that is targeted in one embodiment according to the present invention is an RNA genome in any strain of SARS-CoV-2. Illustrative examples of such a strain include main strains of an L type and an S type, as well as substrains thereof. For the SARS-CoV-2 genome, RNA genomes are reported in many strains. For example, the SARS-CoV-2 genomes of many strains can be referred to information published in the influenza virus gene database GISAID (Global Initiative on Sharing All Influenza Data) (https://www.gisaid.org/epiflu-applications/next-hcov-19-app/).

LAMP (Loop-mediated Isothermal Amplification) method is a method that can amplify the targeted nucleic acid by an isothermal reaction. The LAMP method is characterized by that a targeted nucleic acid can be specifically amplified by means of four or more primers comprising six regions.

The LAMP primers can be designed such that they can be bound to specific regions in the targeted RNA and the cDNA thereof in the SARS-CoV-2 genome. Upon designing the LAMP primers, the regions designated as F3c region, F2c region, F1c region, B1 region, B2 region, and B3 region are specified in the target RNA (in a direction from 3' to 5' side), as well as the regions designated as F3 region, F2 region, F1 region, B1c region, B2c region, and B3c region are specified in the cDNA (in a direction from 5' to 3' side). Here, the F1 region and the F1c region, the F2 region and the F2c region, the F3 region and the F3c region, the B1 region and the B1c region, the B2 region and the B2c region, and the B3 region and the B3c region each are the regions of the complementary nucleotide sequences to each other.

Figure 6:
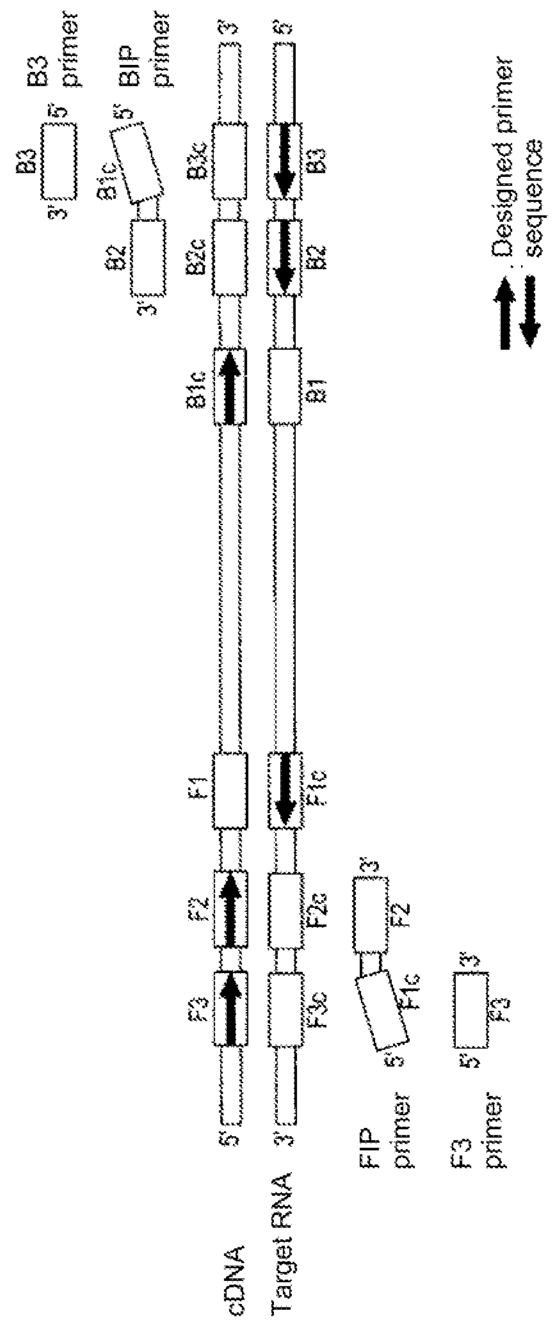
FIG. 6 illustrates a relationship between a target nucleic acid and four LAMP primers.

The LAMP primers include the F3 primer, the B3 primer, the FIP primer, and the BIP primer (FIG. 6). The F3 primer includes the nucleotide sequence of the F3 region. The B3 primer includes the nucleotide sequence of the B3 region. The FIP primer includes the nucleotide sequence of the F1c region and the nucleotide sequence of the F2 region in a direction from 5' to 3' side. The BIP primer includes the nucleotide sequence of the B1c region and the nucleotide sequence of the B2 region from 5' to 3' side. The respective regions in the template nucleic acid corresponding to nucleotide sequences of the primers are indicated by arrows. The direction of the arrow indicates the direction of the corresponding primer on each of the nucleotide sequences in which the starting point of the arrow indicates 5'-end and the end point of the arrow indicates 3'-end.

Figure 7:
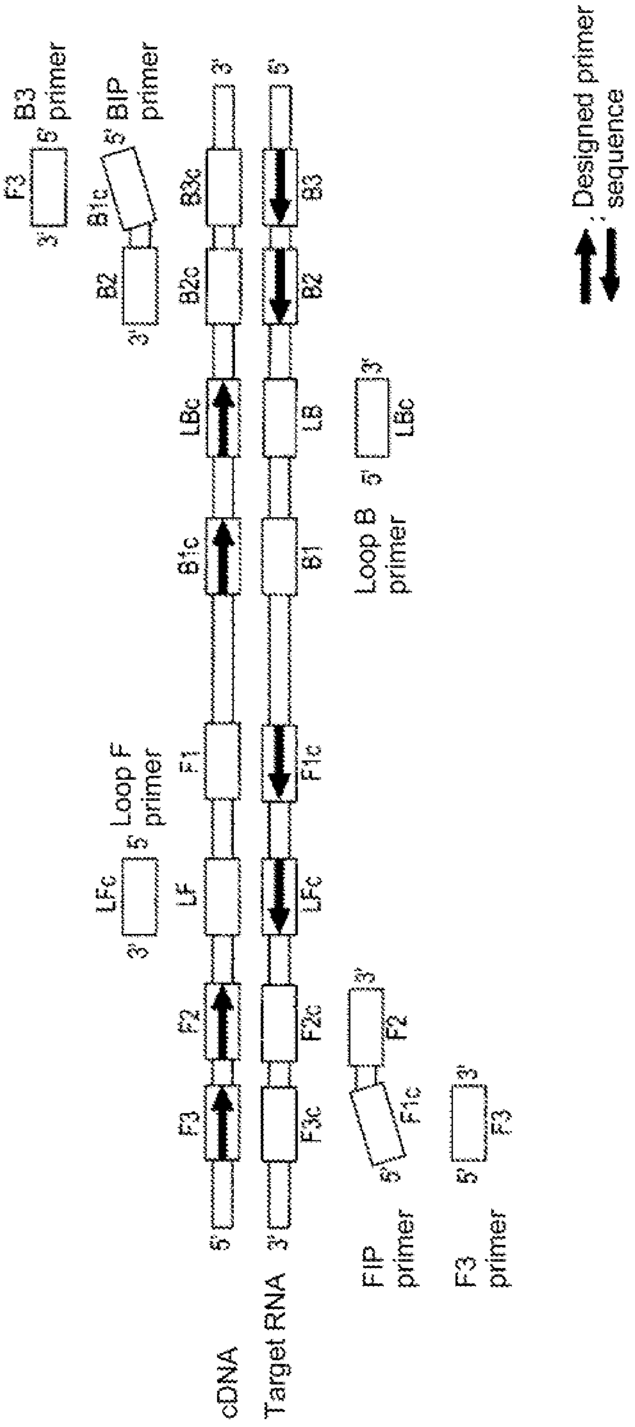
FIG. 7 illustrates a relationship between a target nucleic acid and six LAMP primers.

The LAMP primers may further include the LF primer and/or the LB primer as the loop primer in addition to the F3 primer, the B3 primer, the FIP primer, and the BIP primer (FIG. 7). Concurrent use of the loop primer can enhance the amplification efficiency further more. The LF primer and the LB primer can include the nucleotide sequences of the LFc region and the LB region, respectively. The loop primer can be designed so as to be bound to the loop portion of the amplified product. Illustrative examples of the loop portion include the range of the nucleotide residues from 5'-end of the F2c region to 3' side of 3'-end of the F1c region, and the range of the nucleotide residues from 3'-end of the B2 region to 5' side of 5'-end in the B1 region.

The LAMP primers may include at least 13 continuous nucleotide residues in nucleotide sequences of the aforementioned regions or in nucleotide sequences complementary thereto. The LAMP primers may include at least 14, 15, 16, 17, 18, 19, 20, 21, 22, 23, 24, or 25 continuous nucleotide residues in nucleotide sequences of the aforementioned regions or the nucleotide sequences complementary thereto.

In one embodiment, the one or more ORF regions to be targeted include the Orf1b. The reported nucleotide sequence that encodes the Orf1b is the nucleotide sequence of SEQ ID NO:1 (corresponding to the nucleotide residues at positions 13,468 to 21,555 in GenBank accession number: MN908947). Viruses readily mutate at the rapid evolution speed so that many mutations easily accumulate. On the other hand, the nucleotide sequences that are identical only less than 90% can be regarded from virology that these nucleotide sequences are not derived from the same virus. On the basis of such a viewpoint, in order to avoid the cross-reactivity with a different virus (e.g., SARS-CoV) while covering difference in genome sequences that can be generated among SARS-CoV-2 strains, the LAMP primers can be designed on the basis of a nucleotide sequence showing 90% or more identity to nucleotide sequences in the targeted region. Therefore, when the Orf1b is targeted, the LAMP primers can be designed on the basis of the nucleotide sequence showing 90% or more identity to the nucleotide sequence of SEQ ID NO:1.

Preferably, the target on the Orf1b is the first partial region in the ORF1b corresponding to a nucleotide sequence showing 90% or more identity to the nucleotide sequence of SEQ ID NO:3 (245 base length), or the second partial region in the ORF1b corresponding to a nucleotide sequence showing 90% or more identity to the nucleotide sequence of SEQ ID NO:5 (256 base length). To such a first partial region, the F3 primer, the B3 primer, the FIP primer, and the BIP primer (e.g., four primers comprising the nucleotide sequences of SEQ ID NOs:19-22 or the nucleotide sequences complementary thereto, respectively), as well as, if necessary, the LF primer and the LB primer (e.g., two loop primers comprising the nucleotide sequences of SEQ ID NOs:23 and 24 or the nucleotide sequences complementary thereto, respectively) can be designed. Also, to such a second partial region, the F3 primer, the B3 primer, the FIP primer, and the BIP primer (e.g., four primers comprising the nucleotide sequences of SEQ ID NOs:13-16 or the nucleotide sequences complementary thereto), as well as, if necessary, the LF primer and the LB primer (e.g., two loop primers comprising the nucleotide sequences of SEQ ID NOs:17 and 18 or the nucleotide sequences complementary thereto, respectively) can be designed.

In another embodiment, the one or more ORF regions to be targeted include the OrfM. The reported nucleotide sequence that encodes the OrfM is the nucleotide sequence of SEQ ID NO:6 (corresponding to the nucleotide residues at positions 26,523 to 27,191 in GenBank accession number: MN908947). When the OrfM is targeted, the LAMP primer can be designed on the basis of a nucleotide sequence showing 90% or more identity to the nucleotide sequence of SEQ ID NO:6.

Preferably, the target on the OrfM is the partial region in the OrfM corresponding to a nucleotide sequence showing 90% or more identity to the nucleotide sequence of SEQ ID NO:7 (215 base length). To such a partial region, the F3 primer, the B3 primer, the FIP primer, and the BIP primer (e.g., four primers comprising the nucleotide sequences of SEQ ID NOs:25-28 or sequences complementary thereto, respectively), as well as, if necessary, the LF primer and the LB primer (e.g., two loop primers comprising the nucleotide sequences of SEQ ID NOs:29 and 30 or sequences complementary thereto, respectively) can be designed.

In still another embodiment, the one or more ORF regions to be targeted include the OrfN. The reported nucleotide sequence that encodes the OrfN is the nucleotide sequence of SEQ ID NO:8 (corresponding to the nucleotide residues at positions 28,274 to 29,533 in GenBank accession number: MN908947). When the OrfN is targeted, the LAMP primer can be designed on the basis of a nucleotide sequence showing 90% or more identity to the nucleotide sequence of SEQ ID NO:8.

Preferably, the target on the OrfN is the partial region in the OrfN corresponding to a nucleotide sequence showing 90% or more identity to the nucleotide sequence of SEQ ID NO:9 (231 base length). To such a partial region, the F3 primer, the B3 primer, the FIP primer, and the BIP primer (e.g., four primers comprising the nucleotide sequences of SEQ ID NOs:31-34 or sequences complementary thereto, respectively), as well as, if necessary, the LF primer and the LB primer (e.g., two loop primers comprising the nucleotide sequences of SEQ ID NOs:35 and 36 or sequences complementary thereto, respectively) can be designed.

In still another embodiment, the one or more ORF regions to be targeted include the OrfS. The reported nucleotide sequence that encodes the OrfS is the nucleotide sequence of SEQ ID NO:10 (corresponding to the nucleotide residues at positions 21,563 to 25,384 in GenBank accession number: MN908947). When the OrfS is targeted, the LAMP primers can be designed on the basis of the nucleotide sequence showing 90% or more identity to the nucleotide sequence of SEQ ID NO:10.

Preferably, the target on the OrfS is the first partial region in the OrfS corresponding to a nucleotide sequence showing 90% or more identity to the nucleotide sequence of SEQ ID NO:11 (229 base length), or the second partial region in the OrfS corresponding to the nucleotide sequence showing 90% or more identity to the nucleotide sequence of SEQ ID NO:12 (266 base length). To such a first partial region, the F3 primer, the B3 primer, the FIP primer, and the BIP primer (e.g., four primers comprising the nucleotide sequences of SEQ ID NOs:37-40 or sequences complementary thereto, respectively), as well as, if necessary, the LF primer and the LB primer (e.g., two loop primers comprising the nucleotide sequences of SEQ ID NOs:41 and 42 or sequences complementary thereto, respectively) can be designed. Also, to such a second partial region, the F3 primer, the B3 primer, the FIP primer, and the BIP primer (e.g., four primers comprising the nucleotide sequences of SEQ ID NOs:43-46 or sequences complementary thereto, respectively), as well as, if necessary, the LF primer and the LB primer (e.g., two loop primers comprising the nucleotide sequences of SEQ ID NOs:47 and 48 or sequences complementary thereto, respectively) can be designed.

In a specific embodiment, the primer set including the LAMP primers targeting the one or more ORF regions may be specified so as to include four primers described by the following (a) to (d), and if necessary, two loop primers described by the following (e) to (f):

(a) a first primer that includes a nucleotide sequence consisting of at least 13 continuous nucleotide residues in the F3 region in the one or more ORF regions, or nucleotide sequence complementary thereto (corresponding to the F3 primer or primer complementary thereto);

(b) a second primer that includes a nucleotide sequence consisting of at least 13 continuous nucleotide residues in the B3 region in the one or more ORF regions, or nucleotide sequence complementary thereto (corresponding to the B3 primer or primer complementary thereto);

(c) a third primer that includes a nucleotide sequence consisting of at least 13 continuous nucleotide residues in the F1c region and a nucleotide sequence consisting of at least 13 continuous nucleotide residues in the F2 region in a direction from 5' to 3' side in the one or more ORF regions, or a nucleotide sequence complementary thereto (corresponding to the FIP primer or primer complementary thereto);

(d) a fourth primer that includes a nucleotide sequence consisting of at least 13 continuous nucleotide residues in the B1c region and a nucleotide sequence consisting of at least 13 continuous nucleotide residues in the B2 region in a direction from 5' to 3' side in the one or more ORF regions, or nucleotide sequence complementary thereto (corresponding to the BIP primer or primer complementary thereto);

(e) a fifth primer that includes a nucleotide sequence consisting of at least 13 continuous nucleotide residues in the region (e.g., LFc region) within the range of the nucleotide residues from 5'-end of the F2c region to 3' side of 3'-end of the F1c region in the one or more ORF regions, or nucleotide sequence complementary thereto (corresponding to the LF primer or primer complementary thereto); and (f) a sixth primer that includes a nucleotide sequence consisting of at least 13 continuous nucleotide residues in the region (e.g., LB region) within the range of the nucleotide residues from 3'-end of the B2 region to 5' side of 5'-end of the B1 region in the one or more ORF regions, or nucleotide sequence complementary thereto (corresponding to the LB primer or primer complementary thereto).

In the specific embodiment, when the partial regions in the Orf1b are targeted, it is also preferable to design the first to sixth primers on the basis of the following regions:

(i) F3c region: a nucleotide sequence showing 90% or more identity to the nucleotide sequence consisting of the nucleotide residues at positions 23 to 1 in the nucleotide sequence of SEQ ID NO:2;

(ii) F3 region: a nucleotide sequence complementary to the nucleotide sequence that encodes the F3c region;

(iii) F2c region: a nucleotide sequence showing 90% or more identity to the nucleotide sequence consisting of the nucleotide residues at positions 58 to 40 in the nucleotide sequence of SEQ ID NO:2;

(iv) F2 region: a nucleotide sequence complementary to the nucleotide sequence that encodes the F2c region;

(v) F1c region: a nucleotide sequence showing 90% or more identity to the nucleotide sequence consisting of the nucleotide residues at positions 122 to 98 in the nucleotide sequence of SEQ ID NO:2;

(vi) F1 region: a nucleotide sequence complementary to the nucleotide sequence that encodes the F1c region;

(vii) B1 region: a nucleotide sequence showing 90% or more identity to the nucleotide sequence consisting of the nucleotide residues at positions 175 to 151 in the nucleotide sequence of SEQ ID NO:2;

(viii) B1c region: a nucleotide sequence complementary to the nucleotide sequence that encodes the B1 region;

(ix) B2 region: a nucleotide sequence showing 90% or more identity to the nucleotide sequence consisting of the nucleotide residues at positions 226 to 205 in the nucleotide sequence of SEQ ID NO:2;

(x) B2c region: a nucleotide sequence complementary to the nucleotide sequence that encodes the B2 region;

(xi) B3 region: a nucleotide sequence showing 90% or more identity to the nucleotide sequence consisting of the nucleotide residues at positions 256 to 234 in the nucleotide sequence of SEQ ID NO:2; and (xii) B3c region: a nucleotide sequence complementary to the nucleotide sequence that encodes the B3 region.

More preferably, the first to sixth primers targeting the partial regions in the Orf1b are the six primers comprising the nucleotide sequences of SEQ ID NOs:13-18 or sequences complementary thereto, respectively.

In the specific embodiment, when the partial regions in the Orf1b are targeted, it is also preferable to design the first to sixth primers on the basis of the following regions:

(i) F3c region: a nucleotide sequence showing 90% or more identity to the nucleotide sequence consisting of the nucleotide residues at positions 20 to 1 in the nucleotide sequence of SEQ ID NO:4;

(ii) F3 region: a nucleotide sequence complementary to the nucleotide sequence that encodes the F3c region;

(iii) F2c region: a nucleotide sequence showing 90% or more identity to the nucleotide sequence consisting of the nucleotide residues at positions 50 to 31 in the nucleotide sequence of SEQ ID NO:4;

(iv) F2 region: a nucleotide sequence complementary to the nucleotide sequence that encodes the F2c region;

(v) F1c region: a nucleotide sequence showing 90% or more identity to the nucleotide sequence consisting of the nucleotide residues at positions 105 to 81 in the nucleotide sequence of SEQ ID NO:4;

(vi) F1 region: a nucleotide sequence complementary to the nucleotide sequence that encodes the F1c region;

(vii) B1 region: a nucleotide sequence showing 90% or more identity to the nucleotide sequence consisting of the nucleotide residues at positions 163 to 139 in the nucleotide sequence of SEQ ID NO:4;

(viii) B1c region: a nucleotide sequence complementary to the nucleotide sequence that encodes the B1 region;

(ix) B2 region: a nucleotide sequence showing 90% or more identity to the nucleotide sequence consisting of the nucleotide residues at positions 217 to 199 in the nucleotide sequence of SEQ ID NO:4;

(x) B2c region: a nucleotide sequence complementary to the nucleotide sequence that encodes the B2 region;

(xi) B3 region: a nucleotide sequence showing 90% or more identity to the nucleotide sequence consisting of the nucleotide residues at positions 245 to 224 in the nucleotide sequence of SEQ ID NO:4; and (xii) B3c region: a nucleotide sequence complementary to the nucleotide sequence that encodes the B3 region.

More preferably, the first to sixth primers targeting the partial regions in the Orf1b are the six primers comprising the nucleotide sequences of SEQ ID NOs:19-24 or sequences complementary thereto, respectively.

In the specific embodiment, when the partial regions in the OrfM are targeted, it is also preferable to design the first to sixth primers on the basis of the following regions:

(i) F3c region: a nucleotide sequence showing 90% or more identity to the nucleotide sequence consisting of the nucleotide residues at positions 19 to 1 in the nucleotide sequence of SEQ ID NO:6;

(ii) F3 region: a nucleotide sequence complementary to the nucleotide sequence that encodes the F3c region;

(iii) F2c region: a nucleotide sequence showing 90% or more identity to the nucleotide sequence consisting of the nucleotide residues at positions 39 to 22 in the nucleotide sequence of SEQ ID NO:6;

(iv) F2 region: a nucleotide sequence complementary to the nucleotide sequence that encodes the F2c region;

(v) F1c region: a nucleotide sequence showing 90% or more identity to the nucleotide sequence consisting of the nucleotide residues at positions 97 to 75 in the nucleotide sequence of SEQ ID NO:6;

(vi) F1 region: a nucleotide sequence complementary to the nucleotide sequence that encodes the F1c region;

(vii) B1 region: a nucleotide sequence showing 90% or more identity to the nucleotide sequence consisting of the nucleotide residues at positions 123 to 100 in the nucleotide sequence of SEQ ID NO:6;

(viii) B1c region: a nucleotide sequence complementary to the nucleotide sequence that encodes the B1 region;

(ix) B2 region: a nucleotide sequence showing 90% or more identity to the nucleotide sequence consisting of the nucleotide residues at positions 183 to 165 in the nucleotide sequence of SEQ ID NO:6;

(x) B2c region: a nucleotide sequence complementary to the nucleotide sequence that encodes the B2 region;

(xi) B3 region: a nucleotide sequence showing 90% or more identity to the nucleotide sequence consisting of the nucleotide residues at positions 215 to 195 in the nucleotide sequence of SEQ ID NO:6; and (xii) B3c region: a nucleotide sequence complementary to the nucleotide sequence that encodes the B3 region.

More preferably, the first to sixth primers targeting the partial regions in the OrfM are the six primers comprising the nucleotide sequences of SEQ ID NOs:25-30 or sequences complementary thereto, respectively.

In the specific embodiment, when the partial regions in the OrfN are targeted, it is also preferable to design the first to sixth primers on the basis of the following regions:

(i) F3c region: a nucleotide sequence showing 90% or more identity to the nucleotide sequence consisting of the nucleotide residues at positions 18 to 1 in the nucleotide sequence of SEQ ID NO:8;

(ii) F3 region: a nucleotide sequence complementary to the nucleotide sequence that encodes the F3c region;

(iii) F2c region: a nucleotide sequence showing 90% or more identity to the nucleotide sequence consisting of the nucleotide residues at positions 57 to 37 in the nucleotide sequence of SEQ ID NO:8;

(iv) F2 region: a nucleotide sequence complementary to the nucleotide sequence that encodes the F2c region;

(v) F1c region: a nucleotide sequence showing 90% or more identity to the nucleotide sequence consisting of the nucleotide residues at positions 109 to 87 in the nucleotide sequence of SEQ ID NO:8;

(vi) F1 region: a nucleotide sequence complementary to the nucleotide sequence that encodes the F1c region;

(vii) B1 region: a nucleotide sequence showing 90% or more identity to the nucleotide sequence consisting of the nucleotide residues at positions 143 to 122 in the nucleotide sequence of SEQ ID NO:8;

(viii) B1c region: a nucleotide sequence complementary to the nucleotide sequence that encodes the B1 region;

(ix) B2 region: a nucleotide sequence showing 90% or more identity to the nucleotide sequence consisting of the nucleotide residues at positions 203 to 183 in the nucleotide sequence of SEQ ID NO:8;

(x) B2c region: a nucleotide sequence complementary to the nucleotide sequence that encodes the B2 region;

(xi) B3 region: a nucleotide sequence showing 90% or more identity to the nucleotide sequence consisting of the nucleotide residues at positions 231 to 214 in the nucleotide sequence of SEQ ID NO:8; and (xii) B3c region: a nucleotide sequence complementary to the nucleotide sequence that encodes the B3 region.

More preferably, the first to sixth primers targeting the partial regions in the OrfN are the six primers comprising the nucleotide sequences of SEQ ID NOs:31-36 or sequences complementary thereto, respectively.

In the specific embodiment, when the partial regions in the OrfS are targeted, it is also preferable to design the first to sixth primers on the basis of the following regions:

(i) F3c region: a nucleotide sequence showing 90% or more identity to the nucleotide sequence consisting of the nucleotide residues at positions 18 to 1 in the nucleotide sequence of SEQ ID NO:10;

(ii) F3 region: a nucleotide sequence complementary to the nucleotide sequence that encodes the F3c region;

(iii) F2c region: a nucleotide sequence showing 90% or more identity to the nucleotide sequence consisting of the nucleotide residues at positions 40 to 22 in the nucleotide sequence of SEQ ID NO:10;

(iv) F2 region: a nucleotide sequence complementary to the nucleotide sequence that encodes the F2c region;

(v) F1c region: a nucleotide sequence showing 90% or more identity to the nucleotide sequence consisting of the nucleotide residues at positions 92 to 70 in the nucleotide sequence of SEQ ID NO:10;

(vi) F1 region: a nucleotide sequence complementary to the nucleotide sequence that encodes the F1c region;

(vii) B1 region: a nucleotide sequence showing 90% or more identity to the nucleotide sequence consisting of the nucleotide residues at positions 149 to 125 in the nucleotide sequence of SEQ ID NO:10;

(viii) B1c region: a nucleotide sequence complementary to the nucleotide sequence that encodes the B1 region;

(ix) B2 region: a nucleotide sequence showing 90% or more identity to the nucleotide sequence consisting of the nucleotide residues at positions 200 to 179 in the nucleotide sequence of SEQ ID NO:10;

(x) B2c region: a nucleotide sequence complementary to the nucleotide sequence that encodes the B2 region;

(xi) B3 region: a nucleotide sequence showing 90% or more identity to the nucleotide sequence consisting of the nucleotide residues at positions 229 to 207 in the nucleotide sequence of SEQ ID NO:10; and (xii) B3c region: a nucleotide sequence complementary to the nucleotide sequence that encodes the B3 region.

More preferably, the first to sixth primers targeting the partial regions in the OrfS are the six primers comprising the nucleotide sequences of SEQ ID NOs:37-42 or sequences complementary thereto, respectively.

In the specific embodiment, when the partial regions in the OrfS are targeted, it is also preferable to design the first to sixth primers on the basis of the following regions:

(i) F3c region: a nucleotide sequence showing 90% or more identity to the nucleotide sequence consisting of the nucleotide residues at positions 20 to 1 in the nucleotide sequence of SEQ ID NO:12;

(ii) F3 region: a nucleotide sequence complementary to the nucleotide sequence that encodes the F3c region;

(iii) F2c region: a nucleotide sequence showing 90% or more identity to the nucleotide sequence consisting of the nucleotide residues at positions 59 to 41 in the nucleotide sequence of SEQ ID NO:12;

(iv) F2 region: a nucleotide sequence complementary to the nucleotide sequence that encodes the F2c region;

(v) F1c region: a nucleotide sequence showing 90% or more identity to the nucleotide sequence consisting of the nucleotide residues at positions 114 to 93 in the nucleotide sequence of SEQ ID NO:12;

(vi) F1 region: a nucleotide sequence complementary to the nucleotide sequence that encodes the F1c region;

(vii) B1 region: a nucleotide sequence showing 90% or more identity to the nucleotide sequence consisting of the nucleotide residues at positions 165 to 141 in the nucleotide sequence of SEQ ID NO:12;

(viii) B1c region: a nucleotide sequence complementary to the nucleotide sequence that encodes the B1 region;

(ix) B2 region: a nucleotide sequence showing 90% or more identity to the nucleotide sequence consisting of the nucleotide residues at positions 222 to 199 in the nucleotide sequence of SEQ ID NO:12;

(x) B2c region: a nucleotide sequence complementary to the nucleotide sequence that encodes the B2 region;

(xi) B3 region: a nucleotide sequence showing 90% or more identity to the nucleotide sequence consisting of the nucleotide residues at positions 266 to 243 in the nucleotide sequence of SEQ ID NO:12; and (xii) B3c region: a nucleotide sequence complementary to the nucleotide sequence that encodes the B3 region.

More preferably, the first to sixth primers targeting the partial regions in the OrfS are the six primers comprising the nucleotide sequences of SEQ ID NOs:43-48 or sequences complementary thereto, respectively.

The percent identity to the nucleotide sequences of SEQ ID NOs:1-12 is 90% or more as described above, and preferably 91% or more, 92% or more, 93% or more, 94% or more, 95% or more, 96% or more, 97% or more, 98% or more, 99% or more, or 99.5% or more. The percent identity can be determined by LALIGN according to the algorithm by Huang and Mille (Adv. Appl. Math. (1991) 12: 337-357). LALIGN is open to public in ExPASy, which is Bioinfomatics Resource Portal (https://embnet.vital-it.ch/software/LALIGN_form.htm). Therefore, for convenience, the percent identity can be determined with default setting of LALIGN, which is the program open to public as mentioned above. The default setting of LALIGN is as follows: choose the alignment method: local; number of reported sub-alignments: 3; E-value threshold: 10.0; scoring matrix: BLOSUM 50; opening gap penalty: −12; extending gap penalty: −2.

In the percent identity that is calculated as described above, mutation (namely, substitution, addition, deletion, and insertion, and combinations thereof) of 10% or less of the nucleotide residues relative to the total length of each of the nucleotide sequences of SEQ ID NOs:1-12 is allowed. For example, in the nucleotide sequence showing 90% or more identity to the nucleotide sequence of SEQ ID NO:X, supposing that the total length of the nucleotide sequence of SEQ ID NO:X is the base length of 1,000, mutation up to 100 is allowed; supposing that the total length of the nucleotide sequence of SEQ ID NO:X is the base length of 100, mutation up to 10 is allowed. The number of allowed mutation changes depending on the intended degree of the percent identity and on the intended total length of SEQ ID NO:X; thus, the number is, for example, 100 or less, preferably 80 or less, more preferably 60 or less, still more preferably 40 or less, especially preferably 30 or less, 25 or less, 20 or less, 15 or less, 12 or less, 10 or less, 8 or less, 6 or less, 5, 4, 3, 2, or 1. More specifically, when the aforementioned partial region (256 base length) in the Orf1b is intended as the target, the number of the allowed mutation in the nucleotide sequence showing 90% or more identity to the nucleotide sequence of SEQ ID NO:2 is 25 or less, the number of the allowed mutation in the nucleotide sequence showing 92% or more identity to the nucleotide sequence of SEQ ID NO:2 is 20 or less, the number of the allowed mutation in the nucleotide sequence showing 94% or more identity to the nucleotide sequence of SEQ ID NO:2 is 15 or less, the number of the allowed mutation in the nucleotide sequence showing 96% or more identity to the nucleotide sequence of SEQ ID NO:2 is 10 or less, and the number of the allowed mutation in the nucleotide sequence showing 98% or more identity to the nucleotide sequence of SEQ ID NO:2 is 5 or less.

In a specific embodiment, the primer set may include one or more primer sets selected from the group consisting of the following (A) to (D).

(A) One or more primer sets selected from the group consisting of the following (A1) to (A4) that target the ORF1b:

(A1) four primers comprising the nucleotide sequences of SEQ ID NOs:13-16 or sequences equivalent thereto, or sequences complementary thereto, respectively;

(A2) six primers comprising the nucleotide sequences of SEQ ID NOs:13-18 or sequences equivalent thereto, or sequences complementary thereto, respectively;

(A3) four primers comprising the nucleotide sequences of SEQ ID NOs:19-22 or sequences equivalent thereto, or sequences complementary thereto, respectively; and (A4) six primers comprising the nucleotide sequences of SEQ ID NOs:19-24 or sequences equivalent thereto, or sequences complementary thereto, respectively.

(B) One or more primer sets selected from the group consisting of the following (B1) and (B2) that target the OrfM:

(B1) four primers comprising the nucleotide sequences of SEQ ID NOs:25-28 or sequences equivalent thereto, or sequences complementary thereto, respectively; and (B2) six primers comprising the nucleotide sequences of SEQ ID NOs:25-30 or sequences equivalent thereto, or sequences complementary thereto, respectively.

(C) One or more primer sets selected from the group consisting of the following (C1) and (C2) that target the OrfN:

(C1) four primers comprising the nucleotide sequences of SEQ ID NOs:31-34 or sequences equivalent thereto, or sequences complementary thereto, respectively; and (C2) six primers comprising the nucleotide sequences of SEQ ID NOs:31-36 or sequences equivalent thereto, or sequences complementary thereto, respectively.

(D) One or more primer sets selected from the group consisting of the following (D1) to (D4) that target the OrfS:

(D1) four primers comprising the nucleotide sequences of SEQ ID NOs:37-40 or sequences equivalent thereto, or sequences complementary thereto, respectively;

(D2) six primers comprising the nucleotide sequences of SEQ ID NOs:37-42 or sequences equivalent thereto, or sequences complementary thereto, respectively;

(D3) four primers comprising the nucleotide sequences of SEQ ID NOs:43-46 or sequences equivalent thereto, or sequences complementary thereto, respectively; and (D4) six primers comprising the nucleotide sequences of SEQ ID NOs:43-48 or sequences equivalent thereto, or sequences complementary thereto, respectively.

The equivalent sequence is the nucleotide sequence comprising modification of 1 to 5 nucleotides (preferably 1 to 3 nucleotides, more preferably 1 or 2 nucleotides, still more preferably 1 nucleotide) in the subject nucleotide sequence, wherein the mutation is selected from the group consisting of substitution, addition, deletion, and insertion.

In a specific preferable embodiment, the primer set may include one or more primer sets selected from the group consisting of the following (A') to (D').

(A') One or more primer sets selected from the group consisting of the following (A1') to (A4') that target the ORF1b:

(A1') four primers comprising the nucleotide sequences of SEQ ID NOs:13-16 or sequences complementary thereto, respectively;

(A2') six primers comprising the nucleotide sequences of SEQ ID NOs:13-18 or sequences complementary thereto, respectively;

(A3') four primers comprising the nucleotide sequences of SEQ ID NOs:19-22 or sequences complementary thereto, respectively; and (A4') six primers comprising the nucleotide sequences of SEQ ID NOs:19-24 or sequences complementary thereto, respectively.

(B') One or more primer sets selected from the group consisting of the following (B1') to (B2') that target the OrfM:

(B1') four primers comprising the nucleotide sequences of SEQ ID NOs:25-28 or sequences complementary thereto, respectively; and (B2') six primers comprising the nucleotide sequences of SEQ ID NOs:25-30 or sequences complementary thereto, respectively.

(C') One or more primer sets selected from the group consisting of the following (C1') to (C2') that target the OrfN:

(C1') four primers comprising the nucleotide sequences of SEQ ID NOs:31-34 or sequences complementary thereto, respectively; and (C2') six primers comprising the nucleotide sequences of SEQ ID NOs:31-36 or sequences complementary thereto, respectively.

(D') One or more primer sets selected from the group consisting of the following (D1') to (D4') that target the OrfS:

(D1') four primers comprising the nucleotide sequences of SEQ ID NOs:37-40 or sequences complementary thereto, respectively;

(D2') six primers comprising the nucleotide sequences of SEQ ID NOs:37-42 or sequences complementary thereto, respectively;

(D3') four primers comprising the nucleotide sequences of SEQ ID NOs:43-46 or sequences complementary thereto, respectively; and (D4') six primers comprising the nucleotide sequences of SEQ ID NOs:43-48 or sequences complementary thereto, respectively.

Among the one or more ORF regions, the Orf1b is preferable as the target, and the partial region (SEQ ID NO:5) of the Orf1b is especially preferable as the target. By using the Orf1b or the partial region thereof (SEQ ID NO:5) as the target, SARS-CoV-2 can be detected with high sensitivity.

In addition, one embodiment according to the present invention relates to a method of testing SARS-CoV-2. The method includes detecting SARS-CoV-2 in a specimen obtained from a subject by using the primer set comprising the aforementioned LAMP primers in an RT-LAMP method.

For the subject from which the specimen can be obtained, any subject that can be infected with SARS-CoV-2 may be used. Illustrative examples of such a subject include: mammals (e.g., primates such as a human and a monkey; rodents such as a mouse, a rat, and a rabbit; domestic animals or working animals such as a cow, a pig, a goat, a horse, and sheep; and pets such as a dog and a cat); and birds (e.g., a chicken). Preferably, the subjects are mammals such as a human. In view of clinical application, the subject is preferably a human.

For the specimen, any biological sample which may include SARS-CoV-2 can be used. Illustrative examples of such a specimen include nasal swab, pharyngeal swab, sputum, saliva, cleaning solutions (e.g., a nasal cleaning solution, a mouth cleaning solution, a bronchial cleaning solution, and a lung cleaning solution), blood (e.g., full blood, plasma, and serum), cerebrospinal fluid, and other specimens (e.g., a specimen that contains infected cells). In view of low invasiveness, and prompt and convenient availability of the specimen which may include much of SARS-CoV-2, the specimen is preferably nasal swab, pharyngeal swab, saliva, or sputum.

The specimen may be subjected to the RNA extraction process (e.g., extraction by an organic solvent such as phenol/chloroform or extraction by a commercially available kit) before this is subjected to the RT-LAMP method; alternatively, the RNA extraction may also be omitted. When the RNA extraction is omitted and the specimen is directly subjected to the RT-LAMP method, SARS-CoV-2 can be detected more promptly. It has been confirmed that SARS-CoV-2 can be detected with high sensitivity even when the specimen is directly subjected to the RT-LAMP method. When the RNA extraction is omitted and/or when inactivation of the virus is intended, the specimen may be heated. For example, the specimen may be subjected to the RT-LAMP method after the following procedure; first (1) the specimen is charged into a capped tube, and next (2) the specimen in the tube is heated at high temperature (e.g., 95° C.) for a certain time (e.g., 1 to 30 minutes), and then (3) the specimen is cooled by ice or the like.

The reverse transcription (RT) reaction and the LAMP reaction may be carried out in parallel or separately. In the RT reaction, a reverse transcriptase and a primer for the reverse transcription reaction are required. However, the LAMP primer that is used in the LAMP reaction can also be used as the primer for the reverse transcription reaction. Therefore, in the RT reaction, the LAMP primer may be used as the primer for the reverse transcription reaction. There are many known reverse transcriptases. In one embodiment, any reverse transcriptase may be used as appropriately. For example, the reverse transcriptase (AMV-RT) derived from an avian myeloblastosis virus (AMV) may be used as the reverse transcriptase.

The LAMP reaction can be carried out under any condition in which the target nucleic acids in SARS-CoV-2 can be amplified. The LAMP reaction can amplify the target nucleic acids under an isothermal condition. Therefore, in one embodiment, the LAMP reaction can be carried out under the isothermal condition of, for example, 50 to 80° C. (preferably 60 to 70° C.). The time for the LAMP reaction can be set so as to be long enough for detection of the amplified product (e.g., about 7 to about 10 minutes). In the LAMP reaction, a strand-displacement DNA polymerase is preferably used as the DNA polymerase. In one embodiment, any strand-displacement DNA polymerase can be used appropriately, and a heat-resistant strand-displacement DNA polymerase is preferably used.

The amplified product may be detected by, for example, florescence as an indicator. In this case, the amplified product may be detected by florescence generated by using a reagent which can generate the florescence in response to the presence of the amplified product or amplification reaction (for example, a fluorescence reagent including calcein or an intercalator). The amplified product may be detected, for example, over time or at a specific time after start of the amplification reaction. Amplification of the nucleic acids and detection of the amplified product may be carried out by using an instrument. Amplification of the nucleic acids and detection of the amplified product may be carried out conveniently by a single instrument. For example, the amplified product can be detected conveniently and promptly by using Genelyzer (registered trademark) FIII (manufactured by Canon Medical Systems Corp.).

Determination whether SARS-CoV-2 is included in the specimen can be carried out by, for example, on the basis whether the amplified product is equal to or greater than a prescribed threshold at specific time. For example, when the fluorescence strength equal to or greater than the prescribed value is measured, it is determined that SARS-CoV-2 is included in the specimen. In addition, when the time to reach a prescribed value or more in the measured florescence strength is shorter than the prescribed time, it may be determined that SARS-CoV-2 is included in the specimen. Alternatively, when the RT-LAMP method is carried out by using a commercially available kit, it is also preferable to determine that SARS-CoV-2 is included in the specimen with referring to the condition recommended in an instruction for use attached to the kit.

In a specific embodiment, the method may further include administration of a drug capable of curing the novel coronavirus infectious disease (COVID-19) to the subject that is determined positive to SARS-CoV-2. Illustrative examples of such a drug includes remdesivir, favipiravir, ciclesonide, lopinavir, chloroquine phosphate, hydroxychloroquine, nafamostat, camostat, ivermectin, anti-interleukin-6 receptor antibodies (e.g., sarilumab and tocilizumab), a neutralizing antibody to SARS-CoV-2, and an immunoglobulin formulation (e.g., a formulation including a high concentration pathogen-specific antibody that is taken out from a recovered patient plasma).

One embodiment according to the present invention also relates to: (A) a reagent of testing SARS-CoV-2, comprising the primer set comprising the LAMP primers as described above; and (B) a kit of testing SARS-CoV-2, comprising (1) the primer set comprising the LAMP primers as described above, (2) a strand-displacement DNA polymerase (e.g., a heat-resistant strand-displacement DNA polymerase), and (3) a reverse transcriptase. In addition, the reagent and kit may further include an inorganic pyrophosphatase (e.g., a heat-resistant inorganic pyrophosphatase), a florescence reagent, a substrate such as dNTPs, and a buffer solution. Although the reagent and kit may include these ingredients under separate forms in individual containers (e.g., tubes), two or more ingredients may be mixed in the same container in advance.

EXAMPLES

Hereinafter, some embodiments according to the present invention will be explained in more detail by Examples, but the embodiments are not limited to these Examples.

Example 1

Detection of SARS-CoV-2 by RT-LAMP Method Targeting 6 Regions in SARS-CoV-2 Genome For LAMP primers, six primer sets targeting Orf1b, OrfM, OrfN, and OrfS, which are the ORF regions in the SARS-CoV-2 genome, were designed. The primer sets were designed by referring to the genome sequence of SARS-CoV-2 Wuhan-Hu-1 (GenBank accession number: MN908947). Details of the designed primer sets are listed in Tables 1 to 6. These primer sets were designed so as to amplify the partial regions in the ORF regions indicated by the nucleotide sequences described in FIGS. 1 to 5 (see the underlined portions in FIGS. 1 to 5).

TABLE 1

Primer set targeting Orf1b in SARS-CoV-2 genome (Part 1)

| Primer | Nucleotide sequence |
|---|---|
| F3 | GGTTTTTTCACTTACATTTGTGG (SEQ ID NO: 13) |
| B3 | TCCTCCAAAATATGTAATTTGCA (SEQ ID NO: 14) |
| FIP | GCGAAGTGTCCCATGAGCTTATAAA-CTAGCTCTTGGAGGTTCCG (SEQ ID NO: 15) |
| BIP | AATGCGTCATCATCTGAAGCATTTT-CATAACCATCTATTTGTTCGCG (SEQ ID NO: 16) |
| LF | TCAGCATTCCAAGAATGTTCTGT (SEQ ID NO: 17) |
| LB | ATTGGATGTAATTATCTTGGCAAACC (SEQ ID NO: 18) |

TABLE 2

Primer set targeting Orf1b in SARS-CoV-2 genome (Part 2)

| Primer | Nucleotide sequence |
|---|---|
| F3 | AACCTGAGTTTTATGAGGCT (SEQ ID NO: 19) |
| B3 | TCCTAAGTAAAGTTGAGTCACA (SEQ ID NO: 20) |
| FIP | TGCAAGCACCACATCTTAATGAAGT-CGCATACAGTCTTACAGGCT (SEQ ID NO: 21) |
| BIP | ACGACCATGTCATATCAACATCACA-ACATCACAACCTGGAGCAT (SEQ ID NO: 22) |

TABLE 2-continued

| Primer set targeting Orf1b in SARS-CoV-2 genome (Part 2) | |
|---|---|
| Primer | Nucleotide sequence |
| LF | CAAAGAACACAAGCCCCAAC (SEQ ID NO: 23) |
| LB | GTCTTGTCTGTTAATCCGTATGTTTG (SEQ ID NO: 24) |

TABLE 3

| Primer set targeting OrfM in SARS-CoV-2 genome | |
|---|---|
| Primer | Nucleotide sequence |
| F3 | TTCTTTCAGACTGTTTGCG (SEQ ID NO: 25) |
| B3 | CAGTGATTTCTTTAGGCAGGT (SEQ ID NO: 26) |
| FIP | GGTCAGAATAGTGCCATGGAGTG-TACGCGTTCCATGTGGTC (SEQ ID NO: 27) |
| BIP | ACCGCTTCTAGAAAGTGAACTCGT-CAGCGTCCTAGATGGTGTC (SEQ ID NO: 28) |
| LF | GCACGTTGAGAAGAATGTTAGTTTC (SEQ ID NO: 29) |
| LB | CGGAGCTGTGATCCTTCGT (SEQ ID NO: 30) |

TABLE 4

| Primer set targeting OrfN in SARS-CoV-2 genome | |
|---|---|
| Primer | Nucleotide sequence |
| F3 | GCCAAAAGGCTTCTACGC (SEQ ID NO: 31) |
| B3 | TGGCCTTGTTGTTGTTGG (SEQ ID NO: 32) |
| FIP | CCTACTGCTGCCTGGAGTTGAAT-CAGTCAAGCCTCTTCTCGTTC (SEQ ID NO: 33) |
| BIP | GCTAGAATGGCTGGCAATGGCG-ACATTTTGCTCTCAAGCTGGT (SEQ ID NO: 34) |
| LF | CTTGAACTGTTGCGACTACGTGATG (SEQ ID NO: 35) |
| LB | GCTTTGCTGCTGCTTGACAGAT (SEQ ID NO: 36) |

TABLE 5

| Primer set targeting OrfS in SARS-CoV-2 genome (Part 1) | |
|---|---|
| Primer | Nucleotide sequence |
| F3 | TTGGCAGAGACATTGCTG (SEQ ID NO: 37) |
| B3 | TTAGAACCTGTAGAATAAACACG (SEQ ID NO: 38) |
| FIP | GACACCACCAAAAGAACATGGTG-CTACTGATGCTGTCCGTGA (SEQ ID NO: 39) |
| BIP | CCAGGTTGCTGTTCTTTATCAGGAT-AGGAGTAAGTTGATCTGCATGA (SEQ ID NO: 40) |
| LF | TCAAGAATCTCAAGTGTCTGTGGA (SEQ ID NO: 41) |
| LB | GCACAGAAGTCCCTGTTGCT (SEQ ID NO: 42) |

TABLE 6

| Primer set targeting OrfS in SARS-CoV-2 genome (Part 2) | |
|---|---|
| Primer | Nucleotide sequence |
| F3 | TATTGCTGCTAGAGACCTCA (SEQ ID NO: 43) |
| B3 | CAATAGCACTATTAAATTGGTTGG (SEQ ID NO: 44) |
| FIP | GTACCCGCTAACAGTGCAGAAG-GGCCTTACTGTTTTGCCAC (SEQ ID NO: 45) |
| BIP | CAGGTGCTGCATTACAAATACCATT-TAGAGAACATTCTGTGTAACTCCA (SEQ ID NO: 46) |
| LF | TGAGCAATCATTTCATCTGTGAGC (SEQ ID NO: 47) |
| LB | TGCTATGCAAATGGCTTATAGGTT (SEQ ID NO: 48) |

An artificially synthesized RNA was used as the specimen. The nucleotide sequences of the artificially synthesized RNA correspond to SEQ ID NOs:3, 5, 7, 9, 11, and 12 (here, thymine is changed to uracil). The artificially synthesized RNA was prepared using the DNA that had been synthesized so as to have the nucleotide sequence corresponding to the RNA.

Details of the RT-LAMP method are as follows.

First, a primer mixture solution (2.5 μL) containing the primer set was prepared. The composition of the primer mixture solution is listed in Table 7.

TABLE 7

| Composition of primer mixture solution | | |
|---|---|---|
| Primer | Concentration (μM) | Addition amount (μL) |
| F3 | 100 | 0.05 |
| B3 | 100 | 0.05 |
| FIP | 100 | 0.2 |
| BIP | 100 | 0.2 |
| LF | 100 | 0.1 |
| LB | 100 | 0.1 |
| Rnase-free water | | 1.8 |
| Total | | 2.5 |

Next, a reaction master mix (20 μL) containing the primer mixture solution (2.5 μL) was prepared. The composition of the reaction master mix is listed in Table 8.

TABLE 8

| Composition of reaction master mix (μL) | |
|---|---|
| Isothermal master mix | 15 |
| Reverse transcriptase solution (AMV-RT) | 1 |
| Primer mixture solution | 2.5 |
| Rnase-free water | 1.5 |
| Total | 20 |

The amplification reaction and detection of each of the amplification reaction solutions were carried out by using the isothermal gene amplification detection instrument Genelyzer (registered trademark) FIII (manufactured by Canon Medical Systems Corp.).

Temperature control was carried out as follows.

1) Preheat: 40° C.

2) Amplification: 68° C. (SEQ ID NO:5), 67° C. (SEQ ID NO:3), and 65° C. (SEQ ID NOs:7, 9, 11, and 12).

3) Melt: 95 to 75° C., 0.1° C./second

The template nucleic acids were used under the condition such that the number of the template nucleic acids was 500, 50, 5, or zero (water: negative control) per reaction system. The results are summarized in Table 9.

TABLE 9

Comparison of RT-LAMP method using primers

| | | Copy/reaction | | | |
|---|---|---|---|---|---|
| | | 500 | 50 | 5 | Water |
| Time (min) | Orf1b (SEQ ID NO: 5) | 7.3 | 8.8 | 10.5 | — |
| | Orf1b (SEQ ID NO: 3) | 7.5 | 9.0 | — | — |
| | OrfM (SEQ ID NO: 7) | 8.8 | 11.5 | — | — |
| | OrfN (SEQ ID NO: 9) | 9.5 | 15.8 | — | — |
| | OrfS (SEQ ID NO: 11) | 7.5 | — | — | — |
| | OrfS (SEQ ID NO: 12) | 8.5 | 12.0 | — | — |

As a result, SARS-CoV-2 could be detected in any of the six target ORF regions in the SARS-CoV-2 genome. Among these, SARS-CoV-2 could be satisfactorily detected when the Orf1b was targeted. Especially, when the Orf1b (SEQ ID NO:5) was targeted, SARS-CoV-2 could be detected with high sensitivity. Accordingly, it was confirmed that the ORF region targeted in the RT-LAMP method is preferably Orf1b, and particularly preferably the Orf1b (SEQ ID NO:5).

Example 2

Study of SARS-CoV-2 Detection Sensitivity by RT-LAMP Method (1)

A synthesized RNA (single-strand) having a part of the SARS-CoV-2 genome sequence (256 base length) was used as a template nucleic acid. This template nucleic acid was used under the condition such that the number of the template nucleic acid was 500, 50, 5, or zero (water: negative control) per reaction system.

The RT-LAMP method was carried out in the same way as Example 1. The primer set in the RT-LAMP method targeting the Orf1b (SEQ ID NO:5) in the SARS-CoV-2 genome was used (see Example 1). The results are summarized in Table 10.

TABLE 10

Sensitivity and detection time of RT-LAMP method

ORF1b

| Copy/reaction | 500 | 50 | 5 | Water |
|---|---|---|---|---|
| Time (min) | 7.5 | 9.0 | — | — |
| | 7.3 | 8.8 | 10.5 | — |
| | 8.0 | 11.8 | — | — |
| | 6.8 | 9.3 | | — |
| | 6.8 | 9.0 | — | — |
| | 7.3 | 8.5 | — | — |
| Average | 7.3 | 9.4 | — | — |
| SD | 0.4 | 1.1 | — | — |
| Positive | 6/6 | 6/6 | 1/6 | 0/6 |

As a result, when 50 or more copies of the target RNA were present in the reaction system, the target RNA could be detected with 100% probability. In addition, no non-specific reaction was recognized.

Example 3

Study of SARS-CoV-2 Detection Sensitivity by RT-LAMP Method (2)

A viral RNA (single-strand) having the whole SARS-CoV-2 genome sequence was used as the template nucleic acid.

The viral nucleic acid was serially diluted in order to evaluate to which dilution rate the viral RNA could be still detected.

The sensitivity of the RT-LAMP method was compared with the sensitivity of RT-quantitative PCR (qPCR) method. In the RT-qPCR method, used were (1) one pair of the primers targeting the ORF region (N gene) used for detection of SARS-CoV-2 by National Institute of Infectious Diseases (NIID) of Japan, and one pair of the primers targeting the ORF region (E gene) used for detection of SARS-CoV-2 by World Health Organization (WHO).

TABLE 11

One pair of primers used by NIID

| Primer | Nucleotide sequence |
|---|---|
| Forward | AAATTTTGGGGACCAGGAAC (SEQ ID NO: 49) |
| Reverse | TGGCACCTGTGTAGGTCAAC (SEQ ID NO: 50) |

TABLE 12

One pair of primers used by WHO

| Primer | Nucleotide sequence |
|---|---|
| Forward | ACAGGTACGTTAATAGTTAATAGCGT (SEQ ID NO: 51) |
| Reverse | ATATTGCAGCAGTACGCACACA (SEQ ID NO: 52) |

The RT-LAMP method was carried out in the same way as Example 1. In the RT-LAMP method, the primer set targeting the Orf1b (SEQ ID NO:5) in the SARS-CoV-2 genome was used (see Example 1). The RT-qPCR method was carried out in accordance with the protocol recommended by NIID (Development of Genetic Diagnostic Methods for Novel Coronavirus 2019 (nCoV-2019) in Japan; Advance Publication by J-STAGE; Japanese Journal of Infectious Diseases; Published online: Feb. 18, 2020), and with the protocol recommended by WHO (Diagnostic detection of Wuhan coronavirus 2019 by real-time RT-PCR; -Protocol and preliminary evaluation as of Jan. 13, 2020-). These results are summarized in Table 13.

TABLE 13

Comparison of sensitivity between RT-qPCR method and RT-LAMP method

| | | | Dilution rate of viral RNA | | | | |
|---|---|---|---|---|---|---|---|
| | | | $10^{-2}$ | $10^{-3}$ | $10^{-4}$ | $10^{-5}$ | Water |
| RT-LAMP | Orf1b (SEQ ID NO: 5) | Time (min) | 6.5 | 7.8 | 9.0 | — | — |
| | | | 6.3 | 7.3 | 9.0 | 9.5 | — |
| | | | 6.5 | 7.8 | 12.8 | — | — |
| | | Average | 6.4 | 7.6 | 10.3 | — | — |
| | | SD | 0.1 | 0.2 | 1.8 | — | — |
| | | Positive | 3/3 | 3/3 | 3/3 | 1/3 | 0/3 |
| RT-qPCR | NIID | Ct Value | 30.93 | 34.08 | 37.59 | 39.08 | — |
| | | | 30.79 | 34.12 | 38.05 | 39.34 | — |
| | | | 30.60 | 33.79 | 37.61 | — | — |
| | | Average | 30.77 | 34.00 | 37.75 | 39.21 | — |
| | | SD | 0.14 | 0.15 | 0.21 | 0.13 | — |
| | | Copy/reaction | 2,036.9 | 214.4 | 17.5 | 6.1 | — |
| | | | 2,249.6 | 208.6 | 12.7 | 5.0 | — |
| | | | 2,577.0 | 264.4 | 17.3 | — | — |
| | | Average | 2,287.8 | 229.1 | 15.9 | 5.6 | — |
| | | SD | 222.1 | 25.0 | 2.2 | 0.5 | — |
| | | Positive | 3/3 | 3/3 | 3/3 | 2/3 | 0/3 |
| | WHO | Ct Value | 29.31 | 32.80 | 35.96 | 38.93 | — |
| | | | 29.23 | 32.72 | 35.94 | — | — |
| | | | 29.41 | 32.79 | 35.55 | — | — |
| | | Average | 29.32 | 32.77 | 35.81 | — | — |
| | | SD | 0.07 | 0.03 | 0.19 | — | — |
| | | Copy/reaction | 3,503.2 | 254.9 | 23.7 | 2.6 | — |
| | | | 3,694.3 | 269.0 | 24.1 | — | — |
| | | | 3,246.6 | 256.5 | 32.4 | — | — |
| | | Average | 3,481.4 | 260.2 | 26.7 | — | — |
| | | SD | 183.5 | 6.3 | 4.0 | — | — |
| | | Positive | 3/3 | 3/3 | 3/3 | 1/3 | 0/3 |

As a result, the RT-LAMP method could detect viral RNA with 100% probability to the dilution level of $10^{-4}$ (about 20 copies), which was similar to the RT-qPCR methods (NIID and WHO). In addition, the RT-LAMP method could detect the viral RNA at the dilution level of $10^{-4}$ dilution in a time as short as about 10 minutes. On the other hand, the detection times by the RT-qPCR methods of NIID and WHO to reach the Ct values of about 31 and about 29 were 23 minutes and 22 minutes, respectively. Accordingly, it was confirmed that the RT-LAMP method could achieve the same detection sensitivity as the conventional methods with a shorter time than these conventional methods in detection of SARS-CoV-2.

Example 4

Study of Cross-Reactivity with SARS-CoV

The study was carried out as to whether SARS-CoV, which is closely related to SARS-CoV-2, shows the cross-reactivity with SARS-CoV-2 in the RT-LAMP method using the primer set targeting the Orf1b (SEQ ID NO:5). The viral RNA (single-strand) having the whole SARS-CoV or SARS-CoV-2 genome sequences was used as the template nucleic acid. The RT-LAMP method was carried out in the same way as Example 1. The RT-qPCR for detecting SARS-CoV was carried out in accordance with the protocol recommended by WHO. The results are summarized in Table 14

TABLE 14

Cross-reactivity to SARS-CoV in RT-LAMP method

| | | SARS-CoV | | SARS-CoV-2 |
|---|---|---|---|---|
| RT-LAMP (min) | ORF1b (SEQ ID NO: 5) | — | — | 11.5 |
| RT-qPCR (Ct) | WHO | +(27.5) | +(27.7) | |

As a result, in the RT-LAMP method, the cross-reactivity with SARS-CoV was not confirmed.

Example 5

Study of Direct RT-LAMP Method

In many of the conventional testing methods, extraction of RNA from a specimen is necessary. In extraction of RNA, however, not only expensive RNA extraction kit and equipment but also a skilled technic with a certain level is necessary. In addition, a time of about 30 minutes to about 1 hour is necessary for extraction of RNA. Therefore, this study was carried out as to whether the patient's specimen can be used directly in a amplification reaction without RNA extraction.

The method was carried out as follows. First, in the specimen that was a mixture of nasal swab and pharyngeal swab taken from a healthy subject, SARS-CoV-2 was serially diluted and heated at 95° C. for 10 minutes to inactivate the virus. Next, by using the primer set targeting the partial region (SEQ ID NO:5) in the Orf1b, the study was carried out to which dilution rate level the viral RNA could be detected. In the direct RT-LAMP, heated specimen was used as a template directly in the amplification reaction. The usual RT-LAMP was carried out in the same way as Example 1 to compare the sensitivities. The sensitivity was further compared with the RT-qPCR method (NIID). At this time, in the direct RT-qPCR, the heated specimen was used as the template directly in the amplification reaction of RT-qPCR. These results are summarized in Tables 15 and 16. The nasal swab and the pharyngeal swab used in Tables 15 and 16 were taken out from the same subject in different dates.

TABLE 15

Detection sensitivity of direct RT-LAMP method (1)

| | | | Dilution rate of virus | | | | | | |
|---|---|---|---|---|---|---|---|---|---|
| | Template | | $10^{-2}$ | $10^{-3}$ | $10^{-4}$ | $10^{-5}$ | $10^{-6}$ | $10^{-7}$ | Water |
| Direct RT-LAMP | Heated specimen | Time (min) | 5.5 | 6.0 | 6.8 | 7.5 | 10.5 | — | — |
| | | | 5.3 | 6.0 | 6.8 | 7.3 | 9.0 | 10.5 | — |
| | | | 5.5 | 6.0 | 7.3 | 7.5 | 9.0 | — | — |
| | | Average | 5.4 | 6.0 | 6.9 | 7.4 | 9.5 | — | — |
| | | SD | 0.1 | 0.0 | 0.2 | 0.1 | 0.7 | — | — |
| | | Positive | 3/3 | 3/3 | 3/3 | 3/3 | 3/3 | 1/3 | 0/3 |

TABLE 15-continued

Detection sensitivity of direct RT-LAMP method (1)

| | Template | | Dilution rate of virus $10^{-2}$ | $10^{-3}$ | $10^{-4}$ | $10^{-5}$ | $10^{-6}$ | $10^{-7}$ | Water |
|---|---|---|---|---|---|---|---|---|---|
| RT-LAMP | RNA | Time (min) | 4.3 | 5.0 | 5.8 | 6.5 | 7.3 | — | — |
| | | | 5.5 | 6.0 | 7.3 | 7.5 | 9.0 | — | — |
| | | | 4.8 | 5.8 | 6.3 | 6.8 | 7.5 | 9.5 | — |
| | | Average | 4.8 | 5.6 | 6.4 | 6.9 | 7.9 | — | — |
| | | SD | 0.5 | 0.4 | 0.6 | 0.4 | 0.8 | — | — |
| | | Positive | 3/3 | 3/3 | 3/3 | 3/3 | 3/3 | 1/3 | 0/3 |
| Direct RT-qPCR | Heated specimen | Ct value | 23.14 | 26.47 | 29.86 | 33.43 | 36.40 | — | — |
| | | | 23.22 | 26.50 | 29.87 | 33.29 | 36.93 | — | — |
| | | | 23.01 | 26.46 | 29.75 | 33.28 | 36.96 | — | — |
| | | Average | 23.12 | 26.48 | 29.83 | 33.34 | 36.76 | — | — |
| | | SD | 0.09 | 0.02 | 0.05 | 0.07 | 0.26 | — | — |
| | | Copy/reaction | 1.14E+06 | 9.07E+04 | 6.92E+03 | 4.62E+02 | 4.87E+01 | — | — |
| | | | 1.06E+06 | 8.84E+04 | 6.89E+03 | 5.12E+02 | 3.25E+01 | — | — |
| | | | 1.25E+06 | 9.15E+04 | 7.50E+03 | 5.17E+02 | 3.17E+01 | — | — |
| | | Average | 1.15E+06 | 9.02E+04 | 7.10E+03 | 4.97E+02 | 3.77E+01 | — | — |
| | | SD | 7.73E+04 | 1.30E+03 | 2.81E+02 | 2.49E+01 | 7.85E+00 | — | — |
| | | Positive | 3/3 | 3/3 | 3/3 | 3/3 | 3/3 | 0/3 | 0/3 |
| RT-qPCR | RNA | Ct value | 20.89 | 24.29 | 27.76 | 31.13 | 34.70 | 38.95 | — |
| | | | 20.97 | 24.34 | 27.80 | 31.18 | 34.35 | 37.66 | — |
| | | | 20.75 | 24.28 | 27.65 | 31.00 | 34.51 | 38.16 | — |
| | | Average | 20.87 | 24.30 | 27.74 | 31.10 | 34.52 | 38.26 | — |
| | | SD | 0.09 | 0.03 | 0.07 | 0.07 | 0.14 | 0.53 | — |
| | | Copy/reaction | 6.23E+06 | 4.75E+05 | 3.41E+04 | 2.64E+03 | 1.77E+02 | 7.03E+00 | — |
| | | | 5.85E+06 | 4.56E+05 | 3.29E+04 | 2.55E+03 | 2.29E+02 | 1.87E+01 | — |
| | | | 6.93E+06 | 4.77E+05 | 3.72E+04 | 2.92E+03 | 2.04E+02 | 1.28E+01 | — |
| | | Average | 6.33E+06 | 4.69E+05 | 3.47E+04 | 2.71E+03 | 2.03E+02 | 1.28E+01 | — |
| | | SD | 4.45E+05 | 9.44E+03 | 1.78E+03 | 1.56E+02 | 2.14E+01 | 4.78E+00 | — |
| | | Positive | 3/3 | 3/3 | 3/3 | 3/3 | 3/3 | 3/3 | 0/3 |

TABLE 16

Detection sensitivity of direct RT-LAMP method (2)

| | Template | | Dilution rate of virus $10^{-5}$ | $10^{-6}$ | $2 \times 10^{-6}$ | $4 \times 10^{-6}$ | $8 \times 10^{-6}$ | $10^{-7}$ | Water |
|---|---|---|---|---|---|---|---|---|---|
| Direct RT-LAMP | Heated specimen | Time (min) | 7.5 | 7.8 | 12.5 | 9.3 | — | — | — |
| | | | 7.3 | 9.3 | 10.0 | — | 9.0 | — | — |
| | | | 7.0 | 12.5 | 11.8 | — | — | — | — |
| | | Average | 7.3 | 9.8 | 11.4 | — | — | — | — |
| | | SD | 0.2 | 2.0 | 1.0 | — | — | — | — |
| | | Positive | 3/3 | 3/3 | 3/3 | 1/3 | 1/3 | 0/3 | 0/3 |
| RT-LAMP | RNA | Time (min) | 6.8 | 7.8 | 9.0 | 8.8 | 8.8 | 11.3 | — |
| | | | 6.8 | 8.3 | 8.8 | 10.0 | 10.3 | 11.0 | — |
| | | | 6.5 | 8.3 | 8.0 | 8.5 | 12.0 | 9.0 | — |
| | | Average | 6.7 | 8.1 | 8.6 | 9.1 | 10.3 | 10.4 | — |
| | | SD | 0.1 | 0.2 | 0.4 | 0.7 | 1.3 | 1.0 | — |
| | | Positive | 3/3 | 3/3 | 3/3 | 3/3 | 3/3 | 3/3 | 0/3 |
| Direct RT-qPCR | Heated specimen | Ct value | 31.54 | 35.46 | 37.45 | 38.75 | 39.32 | 38.77 | — |
| | | | 32.05 | 35.32 | 36.15 | 36.71 | 39.45 | 38.96 | — |
| | | | 32.17 | 35.45 | 37.12 | 37.72 | 39.33 | 38.27 | — |
| | | Average | 31.92 | 35.41 | 36.90 | 37.73 | 39.37 | — | — |
| | | SD | 0.27 | 0.06 | 0.55 | 0.83 | 0.06 | — | — |
| | | Copy/reaction | 1.47E+03 | 1.08E+02 | 2.88E+01 | 1.21E+01 | 8.29E+00 | 1.20E+01 | — |
| | | | 1.04E+03 | 1.18E+02 | 6.85E+01 | 4.72E+01 | 7.62E+00 | 1.06E+01 | — |
| | | | 9.67E+02 | 1.09E+02 | 3.58E+01 | 2.40E+01 | 8.23E+00 | 1.67E+01 | — |
| | | Average | 1.16E+03 | 1.12E+02 | 4.44E+01 | 2.78E+01 | 8.05E+00 | 1.31E+01 | — |
| | | SD | 2.20E+02 | 4.69E+00 | 1.73E+01 | 1.46E+01 | 3.03E-01 | 2.61E+00 | — |
| | | Positive | 3/3 | 3/3 | 3/3 | 3/3 | 3/3 | 3/3 | 0/3 |
| RT-qPCR | RNA | Ct value | 30.89 | 34.66 | 35.51 | 35.76 | 37.55 | 37.09 | — |
| | | | 30.98 | 34.20 | 36.33 | 35.97 | 37.67 | 37.97 | — |
| | | | 30.86 | 34.40 | 35.60 | 36.12 | 38.02 | 37.61 | — |
| | | Average | 30.91 | 34.42 | 35.81 | 35.95 | 37.75 | 37.55 | — |
| | | SD | 0.05 | 0.19 | 0.36 | 0.15 | 0.20 | 0.36 | — |

TABLE 16-continued

Detection sensitivity of direct RT-LAMP method (2)

| Template | | Dilution rate of virus | | | | | | |
|---|---|---|---|---|---|---|---|---|
| | | $10^{-5}$ | $10^{-6}$ | $2 \times 10^{-6}$ | $4 \times 10^{-6}$ | $8 \times 10^{-6}$ | $10^{-7}$ | Water |
| | Copy/reaction | 2.27E+03 | 1.84E+02 | 1.05E+02 | 8.83E+01 | 2.69E+01 | 3.66E+01 | — |
| | | 2.13E+03 | 2.50E+02 | 6.08E+01 | 7.71E+01 | 2.49E+01 | 2.04E+01 | — |
| | | 2.30E+03 | 2.18E+02 | 9.83E+01 | 6.95E+01 | 1.97E+01 | 2.58E+01 | — |
| | Average | 2.23E+03 | 2.18E+02 | 8.79E+01 | 7.83E+01 | 2.38E+01 | 2.76E+01 | — |
| | SD | 7.31E+01 | 2.69E+01 | 1.93E+01 | 7.70E+00 | 3.04E+00 | 6.75E+00 | — |
| | Positive | 3/3 | 3/3 | 3/3 | 3/3 | 3/3 | 3/3 | 0/3 |

As a result, the direct RT-LAMP method could detect the virus with 100% probability to the dilution level of $2\times10^{-6}$ (about 90 copies), which was similar to the RT-LAMP method. In addition, the direct RT-LAMP method could detect the virus diluted to the level of $2\times10^{-6}$ in a time as short as about 10 minutes. On the other hand, in the RT-qPCR using the heated specimen, it was found that depending on the condition of the specimen, sensitivity was decreased by about 10 times as compared with the RT-qPCR method using RNA as the template. From these results, it was confirmed that according to the direct RT-LAMP method, the SARS-CoV-2 RNA could be detected satisfactorily and promptly without extracting SARS-CoV-2 RNA from specimen.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

[Sequence Listing]

The invention claimed is:

1. A primer set for detecting SARS-CoV-2, the primer set comprising a plurality of LAMP primers targeting one or more open reading frame (ORF) regions in a SARS-CoV-2 genome, wherein the primer set comprises one or more primer sets selected from the group consisting of the following (1) to (4):

(1) a primer set comprising four primers comprising the nucleotide sequences of SEQ ID NOs:13-16 or the nucleotide sequences complementary thereto, respectively;

(2) a primer set comprising four primers comprising the nucleotide sequences of SEQ ID NOs:19-22 or the nucleotide sequences complementary thereto, respectively;

(3) a primer set comprising four primers comprising the nucleotide sequences of SEQ ID NOs:25-28 or the nucleotide sequences complementary thereto, respectively; and (4) a primer set comprising four primers comprising the nucleotide sequences of SEQ ID NOs:43-46 or the nucleotide sequences complementary thereto, respectively.

2. The primer set according to claim 1, wherein the primer set comprises the primer set of either (1) or (2) or the primer sets of both (1) and (2).

3. The primer set according to claim 1, wherein the primer set comprises the primer set of (1).

4. A method for testing SARS-CoV-2, the method comprising detecting SARS-CoV-2 in a specimen obtained from a subject by using the primer set according to claim 1 in an RT-LAMP method.

5. The method according to claim 4, wherein the specimen is nasal swab, pharyngeal swab, saliva, or sputum.

6. The method according to claim 4, wherein SARS-CoV-2 is detected after heating the specimen.

7. A reagent of testing SARS-CoV-2, comprising the primer set according to claim 1.

8. A kit of testing SARS-CoV-2, comprising the following (1) to (3):

(1) the primer set according to claim 1;

(2) a strand-displacement DNA polymerase; and (3) a reverse transcriptase.

9. A primer set for detecting SARS-CoV-2, the primer set comprising a plurality of LAMP primers targeting one or more open reading frame (ORF) regions in a SARS-CoV-2 genome, wherein the primer set comprises one or more primer sets selected from the group consisting of the following (1) to (4):

(1) a primer set comprising six primers comprising the nucleotide sequences of SEQ ID NOs:13-18 or the nucleotide sequences complementary thereto, respectively;

(2) a primer set comprising six primers comprising the nucleotide sequences of SEQ ID NOs:19-24 or the nucleotide sequences complementary thereto, respectively;

(3) a primer set comprising six primers comprising the nucleotide sequences of SEQ ID NOs:25-30 or the nucleotide sequences complementary thereto, respectively; and (4) a primer set comprising six primers comprising the nucleotide sequences of SEQ ID NOs:43-48 or the nucleotide sequences complementary thereto, respectively.

10. The primer set according to claim 9, wherein the primer set comprises the primer set of either (1) or (2) or the primer sets of both (1) and (2).

11. The primer set according to claim 9, wherein the primer set comprises the primer set of (1).

12. A method for testing SARS-CoV-2, the method comprising detecting SARS-CoV-2 in a specimen obtained from a subject by using the primer set according to claim 9 in an RT-LAMP method.

13. The method according to claim 12, wherein the specimen is nasal swab, pharyngeal swab, saliva, or sputum.

14. The method according to claim 12, wherein SARS-CoV-2 is detected after heating the specimen.

15. A reagent of testing SARS-CoV-2, comprising the primer set according to claim 9.

16. A kit of testing SARS-CoV-2, comprising the following (1) to (3):

(1) the primer set according to claim 9;

(2) a strand-displacement DNA polymerase; and (3) a reverse transcriptase.

* * * * *